United States Patent [19]

Hedegaard

[11] 4,072,760
[45] Feb. 7, 1978

[54] BRONCHOSPASMOLYTIC PHENYLETHANOLAMINES

[75] Inventor: Kurt Hedegaard, Horsholm, Denmark

[73] Assignee: Pharmacia AS, Hillerod, Denmark

[21] Appl. No.: 632,211

[22] Filed: Nov. 17, 1975

[30] Foreign Application Priority Data

Nov. 20, 1974 United Kingdom ............... 50190/74

[51] Int. Cl.² ...................... A61K 31/135; C07C 91/22
[52] U.S. Cl. ...................... 424/330; 560/39; 560/21; 560/138; 260/296 R; 260/329 AM; 260/347.7; 260/465 D; 260/465 E; 260/347.4; 260/519; 260/559 R; 260/570.5 C; 260/570.6; 424/263; 424/275; 424/280; 424/304; 424/311; 424/317; 424/324

[58] Field of Search ..................... 260/570.6; 424/330

[56] References Cited

U.S. PATENT DOCUMENTS 3,574,211  4/1971  Keck et al. ................... 260/570.6

FOREIGN PATENT DOCUMENTS 2,305,092  8/1973  Germany ..................... 260/570.6
575,644  2/1946  United Kingdom ............ 260/570.6
986,048  3/1965  United Kingdom ............ 260/570.6

*Primary Examiner*—Leonard Schenkman
*Attorney, Agent, or Firm*—Hubbell, Cohen, Stiefel & Gross

[57] ABSTRACT

Phenylethanolamines of the formula I

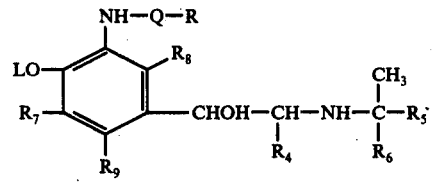

wherein R is substituted phenyl or optionally substituted furyl, thienyl, or pyridyl, $R_5$ is hydrogen, lower alkyl, or optionally substituted benzyl, $R_4$, $R_6$, $R_8$, and $R_9$ each are hydrogen or lower alkyl, $R_7$ is hydrogen, halogen, or lower alkyl, Q is —CO— or —CH$_2$—, and L is hydrogen or lower alkylcarbonyl, and enantiomers, diastereoisomers and salts thereof; also, process for preparing the compounds. Compounds of the invention possess bronchosposmolytic activity.

10 Claims, No Drawings

BRONCHOSPASMOLYTIC PHENYLETHANOLAMINES

The present invention relates to novel phenylethanolamines of the formula I

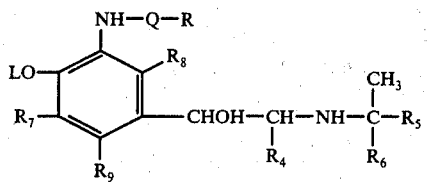

wherein R represents a substituted phenyl group of the formula

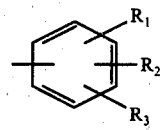

wherein $R_1$, $R_2$, and $R_3$ are the same or different and each represent hydrogen, hydroxy, lower alkylcarbonyloxy, halogen, trifluoromethyl, amino, lower alkylamino, di-lower alkylamino, nitro, carboxy, carbamoyl, lower alkylcarbonyl, lower alkoxycarbonyl, lower alkyl, lower alkoxy, hydroxy-lower alkyl, hydroxy-lower alkoxy, lower alkoxy-lower alkoxy, lower alkylcarbonyl-lower akloxy, lower alkoxycarbonyl-lower alkoxy, carbamoyl-lower alkoxy, amino-lower alkoxy, lower alkylamino-lower alkoxy, di-lower alkylamino-lower alkoxy, cyano-lower alkoxy, carboxy-lower alkoxy, aryl-lower alkoxy, with the proviso that not all of $R_1$, $R_2$, and $R_3$ are hydrogen, or R represents a furyl, thienyl, or pyridyl group, said furyl, thienyl, or pyridyl group optionally being substituted with hydroxy, halogen, nitro, lower alkyl, lower alkoxy, amino, lower alkylamino, or di-lower alkylamino, $R_4$ represents hydrogen or lower alkyl, $R_5$ represents hydrogen, lower alkyl, or optionally substituted benzyl, and $R_6$ represents hydrogen or lower alkyl, $R_7$ represents hydrogen, halogen, or lower alkyl, $R_8$ represents hydrogen or lower alkyl, $R_9$ represents hydrogen or lower alkyl, Q represents —CO— or —CH$_2$—, and L represents hydrogen or lower alkylcarbonyl and enantiomers and, when more than one asymmetric carbon atom is present, also diastereoisomers, and salts thereof, preferably physiologically acceptable salts thereof.

Throughout the present specification and claims, the term "lower alkyl", when used alone or in combination with other groups, designates a straight or branched chain alkyl group preferably containing at most 6 carbon atoms, e.g. methyl, ethyl, isopropyl, and tert.butyl. The term "lower alkoxy", when used alone or in combination with other groups, designates a straight or branched chain alkoxy group preferably containing at most 6 carbon atoms, e.g. methoxy, ethoxy, isopropoxy, and tert.butoxy. As examples of lower alkylcarbonyl groups may be mentioned acetyl, propionyl, isopropylcarbonyl, and tert.butylcarbonyl. As examples of lower alkylcarbonyloxy groups may be mentioned acetoxy, propionyloxy isopropylcarbonyloxy, and tert.butylcarbonyloxy. As examples of lower alkoxycarbonyl groups may be mentioned methoxycarbonyl, ethoxycarbonyl, isopropoxycarbonyl, and tert.butoxycarbonyl. As examples of hydroxy-lower alkyl groups may be mentioned 2-hydroxyethyl, 2-hydroxypropyl, 3-hydroxypropyl, and 2-hydroxy-1-methylethyl. As examples of hydroxy-lower alkoxy groups may be mentioned 2-hydroxyethoxy, 2-hydroxypropoxy, 3-hydroxypropoxy, and 2-hydroxy-1-methylethoxy. As examples of lower alkoxy-lower alkoxy groups may be mentioned methoxymethoxy, 2-methoxyethoxy, and 2-ethoxyethoxy. As examples of lower alkoxycarbonyl-lower alkoxy groups may be mentioned methoxycarbonylmethoxy, 2-methoxycarbonylethoxy, and ethoxycarbonylmethoxy. As examples of carboxy-lower alkoxy groups may be mentioned carboxymethoxy, 1-carboxyethoxy, 2-carboxyethoxy, and 3-carboxy-2-methylpropoxy. As examples of carbamoyl-lower alkoxy groups may be mentioned carbamoylmethoxy, 1- or 2-carbamoylethoxy, and 3-carbamoylpropoxy. As examples of aryl-lower alkoxy groups may be mentioned benzyloxy, phenethoxy, 1-methyl-3-phenylpropoxy, and 1-methyl-2-(p-hydroxyphenyl)ethoxy. As examples of lower alkycarbonyl-lower alkoxy groups may be mentioned acetylmethoxy, 1- or 2-acetylethoxy, propionylmethoxy, 1- or 2-propionylethoxy, and 3-propionylpropoxy. As examples of cyano-lower alkoxy groups may be mentioned cyanomethoxy, 1- or 2-cyanoethoxy, and 3-cyanopropoxy. As examples of lower alkylamino groups may be mentioned methylamino, isopropylamino, tert.butylamino, and hexylamino. As examples of di-lower alkylamino groups may be mentioned N,N-dimethylamino and N-methyl-N-ethylamino. As examples of amino-lower alkoxy groups may be mentioned 2-aminoethoxy and 2- or 3-aminopropoxy. As examples of lower alkylamino-lower alkoxy groups may be mentioned 2-(N-methylamino)ethoxy, 2-(N-ethylamino)ethoxy, 2-(N-isopropylamino)ethoxy, and 2-(N-tert.butylamino)ethoxy. As examples of di-lower alkylamino-lower alkoxy groups may be mentioned 2-(N,N-dimethylamino)ethoxy and 2- or 3-(N,N-dimethylamino)propoxy. As examples of an optionally substituted benzyl group may be mentioned benzyl, and benzyl substituted with hydroxy, lower alkoxy, or alkylenedioxy, such as 4-hydroxybenzyl, and 4-methoxybenzyl, and 3,4-methylendioxybenzyl. The term "halogen" designates chlorine, bromine, and fluorine. Preferred furyl, thienyl, and pyridyl groups R are unsubstituted groups, such as 2-furyl, 2-thienyl, and 2- or 4-pyridyl. The furyl, thienyl, and pyridyl group R may carry substituents, among which hydroxy and especially lower alkoxy and lower alkyl should be mentioned. The lower alkylcarbonyl group L is a group which, in an animal or human body, is readily split off to leave the free hydroxy group, such as acetyl, propionyl, and butyryl and the like.

When R is a substituted phenyl group, it is preferred that $R_1$ and $R_2$ each are hydrogen, and that the substituent $R_3$ is in the 4-position and is an alkoxy or one of the above-defined substituted alkoxy groups.

Preferred compounds of the present invention are compounds of the formula I′

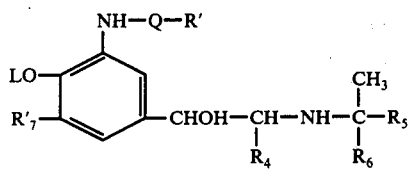

wherein $R_4$, $R_5$, $R_6$, L, and Q each have the above-mentioned meanings, but $R_4$ preferably is hydrogen or methyl, R' represents a group of the formula

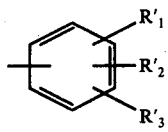

wherein $R'_1$, $R'_2$, and $R'_3$ are the same or different and each represent hydrogen, nitro, hydroxy, lower alkoxy, or any of the substituted lower alkoxy groups stated in the defintion of $R_1$, $R_2$, and $R_3$ in connection with formula I (said alkoxy or substituted alkoxy group preferably being the only substituent on the benzene nucleus and preferably being in the 4-position thereof), with the proviso that not all of $R'_1$, $R'_2$, and $R'_3$ are hydrogen, and $R'_7$ represents hydrogen, chlorine or bromine, and enantiomers and, when more than one asymmetric carbon atom is present, also diastereomers, and salts thereof, preferably physiologically acceptable salts thereof.

Within formula I', a preferred subclass are compounds of formula I"

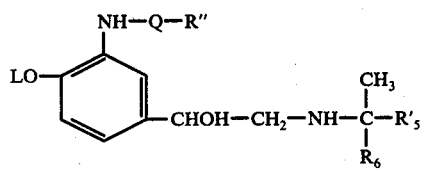

wherein $R_6$, L, and Q each have the above-mentioned meanings, R" designates a 4-alkoxyphenyl group such as 4-ethoxyphenyl, 4-isopropoxyphenyl, 4-tert.butoxyphenyl, or preferably 4-methoxyphenyl, 4-hydroxyphenyl, or 4-nitrophenyl, and $R'_5$ designates isopropyl, tert.butyl, or optionally substituted benzyl, and enantiomers, diastereomers, and salts thereof, preferably physiologically acceptable salts thereof.

Another preferred subcalass within formula I are compounds of formula I'''

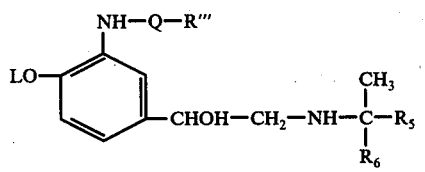

wherein $R_5$, $R_6$, and L each have the above-mentioned meanings, and R''' is 4-ethoxyphenyl, 4-methoxyphenyl, 4-hydroxyphenyl, 4-nitrophenyl, or 4-(2-methoxyethoxy)phenyl, and enantiomers, diastereomers, and salts thereof, preferably physiologically acceptable salts thereof. Among these, an especially preferred compound is 3-(4-methoxybenzylamino)-4-hydroxy-α-(tert.butylaminomethyl)benzylalcohol, in the form of the racemate or either of the enantiomers, and also salts (including di-salts) thereof, e.g. the hydrochloride.

A further interesting subclass of the compounds of the present invention are compounds of the formula I wherein $R_5$ and $R_6$ are each methyl, and enantiomers, diastereomers, and salts thereof, preferably physiologically acceptable salts thereof. The compounds of the present invention show interesting pharmacological properties, in particular due to their affinity to β-adrenergic receptors. Specifically, bronchospasmolytic effect (due to their $β_2$-adrenergic stimulating capacity) has been found. Hence, the compounds of the present invention may be used as medicaments and as entermediates in the preparation of medicaments.

compounds of a structure which is to some extent similar to the compounds of the present invention are described in British Pat. Specification No. 575,644, German Offenlegungsschrift No. 2,305,092 German Offenlegungsschrift No. 2,357,346, and Netherlands Patent No. 85,197. However, the compounds of the present invention differ from these known compounds inter alia in that they contain the readical R being a substituted benzene ring or an optionally substituted furyl, thienyl, or pyridyl group.

The compounds of the present invention may be formulated for administration in any convenient way be analogy with other pharmaceuticals.

Thus, the composition comprising the compounds of the invention may be in the form of pharmaceutical preparations, e.g. in solid, semisolid or liquid form, which contain the active compound of the invention in admixture with a pharmaceutical or inorganic carrier or excipient suitable for enteral or parenteral application. The active ingredient may, e.g., be formulated with the usual carriers for tablets, pellets, capsules, suppositories, solutions, emulsions, aqueous suspensions, inhalastion, e.g. in aerolos dispenser, and other suitable administration forms. Examples of carriers are glucose, lactose, gum acacia, gelatin, mannitol, starch paste, magnesium trisilicate, talc, corn starch, keratin, colloidal silical, potato starch, urea, and other carriers suitable for use in manufacturing compositions in solid, semisolid, or liquid form, and in addition auxiliary, stabilizing, thickening, coloring, flavoring, and preservative agents can be contained in the composition of this invention.

The active compound is included in the compositions of the invention in an amount sufficient to produce the desired therapeutical effect upon administration. The dosage or therapeutically effective quantity of the compound varies and also depends upon the age and condition of each individual patient being treated.

A preferred tablet formulation for oral administration contains 0.1 – 50, preferably 1 – 20, especially 1 – 5, mg of a compound of the present invention per unit dosage which may be administered 1 – 4 times per day or as a sustained release composition.

Mixtures of oral administration preferably contain 0.1 – 1 mg of a compound of the invention per ml. The preferred dosage of such mixtures is 5 – 10 ml 1 – 4 times per day.

For aerosol preparations, the preferred dose unit (puff) is 10 – 500 micrograms per puff.

Injection preparations preferably contain 1.0 – 5 mg of a compound of the invention per ml. A preferred injected dose is about 1.0 – 2 ml.

As examples of representative and preferred compounds of the present invention may be mentioned:

3-(4-nitrobenzamido)-4-hydroxy-α-(tert-.butylaminomethyl)benzylalcohol,
3-(3-nitrobenzamido)-4-hydroxy-α-(tert-.butylaminomethyl)benzylalcohol,
3-(2-nitrobenzamido)-4-hydroxy-α-(tert-.butylaminomethyl)benzylalcohol,
3-(4-methoxybenzamido)-4-hydroxy-α-(tert-.butylaminomethyl)benzylalcohol,
3-(4-chlorobenzamido)-4-hydroxy-α-(tert-.butylaminomethyl)benzylalcohol,
3-(3,4-dichlorobenzamido)-4-hydroxy-α-(tert-.butylaminomethyl)benzylalcohol,
3-(4-aminobenzamido)-4-hydroxy-α-(tert-.butylaminomethyl)benzylalcohol,
3-(4-methoxybenzylamino)-4-hydroxy-α-(tert-.butylaminomethyl)benzylalcohol,
3-(4-methylbenzylamino)-4-hydroxy-α-(tert-.butylaminomethyl)benzylalcohol,
3-(4-hydroxybenzylamino)-4-hydroxy-α-(tert-.butylaminomethyl)benzylalcohol,
3-(3,4,5-trimethoxybenzylamino)-4-hydroxy-α-(tert-.butylaminomethyl)benzylalcohol,
3-(2-hydroxybenzylamino)-4-hydroxy-α-(tert-.butylaminomethyl)benzylalcohol,
3-(3,4-dimethoxybenzylamino)-4-hydroxy-α-(tert-.butylaminomethyl)benzylalcohol,
3-(4-nitrobenzylamino)-4-hydroxy-α-(tert-.butylaminomethyl)benzylalcohol,
3-(4-aminobenzylamino)-4-hydroxy-α-(tert-.butylaminomethyl)benzylalcohol,
3-(3-methoxy-4-hydroxybenzylamino)-4-hydroxy-α(tert.butylaminomethyl) benzylalcohol,
3-(2-methoxybenzylamino)-4-hydroxy-α-(tert-.butylaminomethyl)- benzylalcohol,
3-(3-methoxybenzylamino)-4-hydroxy-α-(tert-.butylaminomethyl) benzylalcohol,
3-(3-hydroxybenzylamino)-4-hydroxy-α-(tert-.butylaminomethyl) benzylalcohol,
3-(3,4-dihydroxybenzylamino)-4-hydroxy-α-(tert-.butylaminomethyl) benzylalcohol,
3-(3,5-dihydroxybenzylamino)-4-hydroxy-α-(tert-.butylaminomethyl)benzylalcohol,
3-(3-methyl-4-hydroxybenzylamino)-4-hydroxy-α:(tert.butylaminomethyl)benzylalcohol,
3-(3-chloro-4-hydroxybenzylamino)-4-hydroxy-α-(tert.butylaminomethyl) benzylalcohol,
3-(3-methyl-4-methoxybenzylamino)-4-hydroxy-α-(tert.butylaminomethyl) benzylalcohol,
3-(3,5-dimethyl-4-methoxybenzylamino)-4-hydroxy-α-(tert.butylaminomethyl)benzylalcohol,
3-(3-nitro-4-hydroxybenzylamino)-4-hydroxy-α-(tert.butylaminomethyl)benzylalcohol,
3-(3-bromo-4-hydroxybenzylamino)-4-hydroxy-α-(tert.butylaminomethyl)benzylalcohol,
3-(3,5-dichloro-4-hydroxybenzylamino)-4-hydroxy-α-(tert.butylaminomethyl)benzylalcohol,
3-(4-ethoxybenzylamino)-4-hydroxy-α-(tert-.butylaminomethyl) benzylalcohol,
3-(4-propoxybenzylamino)-4-hydroxy-α-(tert-.butylaminomethyl) benzylalcohol,
3-(4-isopropoxybenzylamino)-4-hydroxy-α-(tert-.butylaminomethyl)benzylalcohol,
3-(4-tert.butoxybenzylamino)-4-hydroxy-α-(tert-.butylaminomethyl)benzylalcohol,
3-(3,4-diethoxybenzylamino)-4-hydroxy-α-(tert-.butylaminomethyl)benzylalcohol,
3-(3-ethoxy-4-hydroxybenzylamino)-4-hydroxy-α-(tert.butylaminomethyl)benzylalcohol,
3-(4-carboxybenzylamino)-4-hydroxy-α-(tert-.butylaminomethyl) benzylalcohol,
3-(4-ethoxycarbonylbenzylamino)-4-hydroxy-α-(tert-.butylaminomethyl) benzylalcohol,
3-(3-carboxy-4-hydroxybenzylamino)-4-hydroxy-α-(tert.butylaminomethyl)benzylalcohol,
3-(4-[N,N-dimethylamino]benzylamino)-4-hydroxy-α-(tert.butylaminomethyl)benzylalcohol,
3-[4-(2-hydroxyethoxy)benzylamino]-4-hydroxy-α-(tert.butylaminomethyl)benzylalcohol,
3-[4-(2-methoxyethoxy)benzylamino]-4-hydroxy-α-(tert.butylaminomethyl)benzylalcohol,
3-[4-(ethoxycarbonylmethoxy)benzylamino]-4-hydroxy-α-(tert.butylaminomethyl)benzylalcohol,
3-[4-(carboxymethoxy)benzylamino]-4-hydroxy-α-(tert.butylaminomethyl)benzylalcohol,
3-[4-(carbamoylmethoxy)benzylamino]-4-hydroxy-α-(tert.butylaminomethyl)benzylalcohol,
3-[4-(2-ethoxyethoxy)benzylamino]-4-hydroxy-α-(tert.butylaminomethyl)benzylalcohol,
3-[4-(2-hydroxypropoxy)benzylamino]-4-hydroxy-α-(tert.butylaminomethyl)benzylalcohol,
3-[4-(acetylmethoxy)benzylamino]-4-hydroxy-α-(tert.butylaminomethyl)benzylalcohol,
3-[4-cyanomethoxy)benzylamino]-4-hydroxy-α-(tert-.butylaminomethyl)benzylalcohol,
3-[4-(2-cyanoethoxy)benzylamino]-4-hydroxy-α-(tert.butylaminomethyl)benzylalcohol,
3-[(5-methoxyfur-2-ylmethyl)amino]-4-hydroxy-α-(tert.butylaminomethyl)benzylalcohol,
3-[(5-methoxythien-2-ylmethyl)amino]-4-hydroxy-α-(tert.butylaminomethyl)benzylalcohol,
3-[(5-methylfur-2-ylmethyl)amino]-4-hydroxy-α-(tert.butylaminomethyl)benzylalcohol,
3-(2-pyridylmethylamino)-4-hydroxy-α-(tert-.butylaminomethyl)benzylalcohol,
3-(4-pyridylmethylamino)-4-hydroxy-α-(tert-.butylaminomethyl)benzylalcohol,
3-(2-furylcarbonylamino)-4-hydroxy-α-(tert-.butylaminomethyl)benzylalcohol,
3-(2-thienylcarbonylamino)-4-hydroxy-α-(tert-.butylaminomethy)benzylalcohol,
3-[(5-methoxyfur-2-yl)carbonylamino]-4-hydroxy-α-(tert.butylaminomethyl)benzylalcohol,
3-[(5-methylthien-2-ylcarbonyl)amino]-4-hydroxy-α-(tert.butylaminomethyl)benzylalcohol,
3-(4-hydroxybenzamido)-4-hydroxy-α-(tert-.butylaminomethyl)benzylalcohol,
3-(3,5-dihydroxybenzamido)-4-hydroxy-α-(tert-.butylaminomethyl)benzylalcohol,
3-(3-methoxybenzamido)-4-hydroxy-α-(tert-.butylaminomethyl)benzylalcohol,
3-(2-methoxybenzamido)-4-hydroxy-α-(tert-.butylaminomethyl)benzylalcohol,
3-(4-ethoxybenzamido)-4-hydroxy-α-(tert-.butylaminomethyl)benzylalcohol.
3-(4-propoxybenzamido)-4-hydroxy-α-(tert-.butylaminomethyl)benzylalcohol,
3-(4-isopropoxybenzamido)-4-hydroxy-α-(tert-.butylaminomethyl) benzylalcohol,
3-(4-tert.butoxybenzamido)-4-hydroxy-α-(tert-.butylaminomethyl)benzylalcohol,
3-(3,4-dimethoxybenzamido)-4-hydroxy-α-(tert-.butylaminomethyl)benzylalcohol,
3-(4-methylbenzamido)-4-hydroxy-α-(tert-.butylaminomethyl)benzylalcohol,
3-(3,4-dimethylbenzamido)-4-hydroxy-α-(tert-.butylaminomethyl)benzylalcohol, 3-(3,5-dimethoxybenzamido)-4-hydroxy-α-(tert.butylaminomethyl)benzylalcohol,
3-(3,4,5-trimethoxybenzamido)-4-hydroxy-α-(tert.butylaminomethyl)benzylalcohol,
3-(4-methoxybenzamido)-4-hydroxy-5-chloro-α-(tert.butylaminomethyl)benzylalcohol,
3-(4-methoxybenzamido)-4-hydroxy-5-bromo-α-(tert.butylaminomethyl)benzylalcohol,
3-(4-ethoxybenzamido)-4-hydroxy-5-chloro-α-(tert.butylaminomethyl)benzylalcohol,
3-(3-chloro-4-methoxybenzamido)-4-hydroxy-5-chloro-α-(tert.butylaminomethyl)benzylalcohol,
3-(3-methyl-4-ethoxybenzamido)-4-hydroxy-5-chloro-α-(tert.butylaminomethyl)benzylalcohol,
3-(3,5-diethoxybenzamido)-4-hydroxy-5-chloro-α-(tert.butylaminomethyl)benzylalcohol,
3-(3-methyl-4-methoxybenzamido)-4-hydroxy-5-chloro-α-(tert.butylaminomethyl)benzylalcohol,
3-(3-chloro-4-methoxy-5-methylbenzamido)-4-hydroxy-5-chloro-α-(tert.butylaminomethyl)benzylalcohol,
3-(4-methoxybenzylamino)-4-hydroxy-5-chloro-α-(tert.butylaminomethyl)benzylalcohol,
3-(4-methoxybenzylamino)-4-hydroxy-5-bromo-α-(tert.butylaminomethyl)benzylalcohol,
3-(4-methoxybenzylamino)-4-hydroxy-2-methyl-α-(tert.butylaminomethyl)benzylalcohol,
3-(4-methoxybenzylamino)-4-hydroxy-5-methyl-α-(tert.butylaminomethyl)benzylalcohol,
3-(4-methoxybenzylamino)-4-hydroxy-2,5-dimethyl-α-(tert.butylaminomethyl)benzylalcohol,
3-[4-(carbamoylmethoxy)benzamido]-4-hydroxy-α-(tert.butylaminomethyl)benzylalcohol,
3-[4-(2-methoxyethoxy)benzamido]-4-hydroxy-α-(tert.butylaminomethyl)benzylalcohol,
3-[4-(2-ethoxyethoxy)benzamido]-4-hydroxy-α-(tert.butylaminomethyl)benzylalcohol,
3-[4-(2-hydroxypropoxy)benzamido]-4-hydroxy-α-(tert.butylaminomethyl)benzylalcohol,
3-[4-(acetylmethoxy)benzamido]-4-hydroxy-α-(tert.butylaminomethyl)benzylalcohol,
3-[4-cyanomethoxy)benzamido]-4-hydroxy-α-(tert.butylaminomethyl)benzylalcohol,
3-[4-(2-cyanoethoxy)benzamido]-4-hydroxy-α-(tert.butylaminomethyl)benzylalcohol,
3-(4-methoxybenzylamino)-4-acetoxy-α-(tert.butylaminomethyl)benzylalcohol,
3-(4-methoxybenzylamino)-4-propionyloxy-α-(tert.butylaminomethyl)benzylalcohol,
3-(4-methoxybenzylamino)-4-isobutyryloxy-α-(tert.butylaminomethyl)benzylalcohol,
3-(4-methoxybenzylamino)-4-butyryloxy-α-(tert.butylaminomethyl)benzylalcohol,
3-(4-methoxybenzylamino)-4-hydroxy-α-[1-(tert.butylamino)ethyl]benzylalcohol
3-(4-methoxybenzamido)-4-acetoxy-α-(tert.butylaminomethyl)benzylalcohol,
3-(4-methoxybenzamido)-4-isobutyryloxy-α-(tert.butylaminomethyl)benzylalcohol,
3-(4-ethoxybenzylamino)-4-acetoxy-α-(tert.butylaminomethyl)benzylalcohol,
3-(4-ethoxybenzylamino)-4-isobutyryloxy-α-(tert.butylaminomethyl)benzylalcohol,
3-(4-ethoxybenzylamino)-4-butyryloxy-α-(tert.butylaminomethyl)benzylalcohol,
3-(4-ethoxybenzamido)-4-isobutyryloxy-α-(tert.butylaminomethyl)benzylalcohol,
3-(4-methoxybenzylamino)-4-isobutyryloxy-5-chloro-α-(tert.butylaminomethyl)benzylalcohol,
3-(4-methoxybenzylamino)-4-isobutyryloxy-5-bromo-α-(tert.butylaminomethyl)benzylalcohol,
3-(4-methoxybenzylamino)-4-valeryloxy-α-(tert.butylaminomethyl)benzylalcohol, and all corresponding compounds which in place of the tert.butyl group contain an isopropyl group such as 3-(4-ethoxybenzylamino)-4-hydroxy-α-(isopropylaminomethyl)benzylalcohol,
3-(4-methoxybenzylamino)-4-hydroxy-α-(isopropylaminomethyl)benzylalcohol,
3-(4-hydroxybenzylamino)-4-hydroxy-α-(isopropylaminomethyl)benzylalcohol,
3-(4-nitrobenzylamino)-4-hydroxy-α-(isopropylaminomethyl)benzylalcohol,
3-(2-pyridylmethylamino)-4-hydroxy-α-(isopropylaminomethyl)benzylalcohol,
3-(4-ethoxybenzamido)-4-hydroxy-α-(isopropylaminomethyl)benzylalcohol,
3-(4-methoxybenzamido)-4-hydroxy-α-(isopropylaminomethyl)benzylalcohol,
3-(4-hydroxybenzamido)-4-hydroxy-α-(isopropylaminomethyl)benzylalcohol,
3-(4-nitrobenzamido)-4-hydroxy-α-(isopropylaminomethyl)benzylalcohol,
3-(2-pyridylcarbonylamino)-4-hydroxy-α-(isopropylaminomethyl)benzylalcohol,
3-(4-pyridylcarbonylamino)-4-hydroxy-α-(isopropylaminomethyl)benzylalcohol,
3-(4-methoxybenzylamino)-4-acetoxy-α-(isopropylaminomethyl)benzylalcohol,
3-(4-methoxybenzylamino)-4-propionyloxy-α-(isopropylaminomethyl)benzylalcohol,
3-(4-methoxybenzylamino)-4-isobutyryloxy-α-(isopropylaminomethyl)benzylalcohol,
3-(4-methoxybenzylamino)-4-butyryloxy-α-(isopropylaminomethyl)benzylalcohol,
3-(4-methoxybenzylamino)-4-valeryloxy-α-(isopropylaminomethyl)benzylalcohol,
3-(4-methoxybenzamido)-4-acetoxy-α-(isopropylaminomethyl)benzylalcohol,
3-(4-methoxybenzamido)-4-isobutyryloxy-α-(isopropylaminomethyl)benzylalcohol,
3-(4-methoxybenzamido)-4-isobutyryloxy-5-chloro-α-(isopropylaminomethyl)benzylalcohol,
3-(4-methoxybenzylamino)-4-isobutyryloxy-5-chloro-α-(isopropylaminomethyl)benzylalcohol,
3-(4-methoxybenzylamino)-4-butyryloxy-5-chloro-α-(isopropylaminomethyl)benzylalcohol,
3-(4-methoxybenzylamino)-4-propionyloxy-5-chloro-α-(isopropylaminomethyl)benzylalcohol, and all the corresponding compounds which in place of the tert. butyl group contain an α,α-dimethylphenethyl group such as 3-(4-methoxybenzylamino)-4-hydroxy-α-(α,α-dimethylphenetylaminomethyl)benzylalcohol,
3-(4-ethoxybenzylamino)-4-hydroxy-α-(α,α-dimethylphenetylaminomethyl)benzylalcohol,
3-(4-methoxybenzamido)-4-hydroxy-α-(α,α-dimethylphenetylaminomethyl)benzylalcohol,
3-(3,4-dimethoxybenzylamino)-4-hydroxy-α-(α,α-dimethylaminophenetylaminomethyl)benzylalcohol, and all the corresponding compounds which in place of the tert.butyl group contain a 1-methyl-2-(4-methoxyphenyl)ethyl group such as 3-(4-methoxybenzylamino)-4-hydroxy-α-(1-methyl-2-[4-methoxyphenyl]ethylaminomethyl)benzylalcohol, 3-(4-ethoxybenzylamino)-4-hydroxy-α-(1methyl-2[4-methoxyphenyl]ethylaminomethyl)benzylalcohol, 3-(4-methoxybenzamido)-4-hydroxy-α-(1-methyl-2-[4-methoxyphenyl]ethylaminomethyl)benzylalcohol, 3-(3,4-dimethoxybenzylamino)-4-hydroxy-α-(1-methyl-2-]4-methoxyphenyl]ethylaminomethyl)benzylalcohol, and all corresponding compounds which in place of the tert.butyl group contain a 1-methyl-2-(4-hydroxyphenyl)ethyl group such as 3-(4-methoxybenzylamino)-4-hydroxy-α-(1-methyl-2-[4-hydroxyphenyl]ethylaminomethyl)benzylalcohol, 3-(4-ethoxybenzylamino)-4-hydroxy-α-(1-methyl-2-[4-hydroxyphenyl]ethylaminomethyl)benzylalcohol, 3-(4-methoxybenzamido)-4-hydroxy-α-(1-methyl-2-[4-hydroxyphenyl]ethylaminomethyl)benzylalcohol, 3-(3,4-dimethoxybenzylamino)-4-hydroxy-α-(1-methyl-2-[4-hydroxyphenyl]ethylaminomethyl)benzylalcohol, and physiologically acceptable salts thereof, such as hydrochlorides thereof. According to the present invention, compounds of the formula I and salts thereof may be prepared by various processes, e.g. by:

a. reacting a compound of the formula II

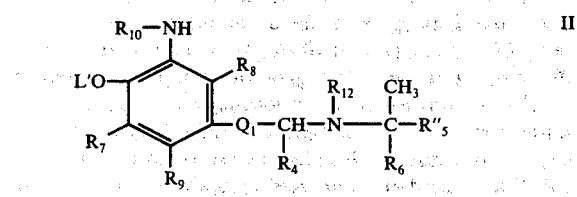

wherein $R_4$, $R_6$, $R_7$, $R_8$, and $R_9$ each have the above-mentioned meanings, and $R''_5$ and $L'$, respectively, each have the same meaning as $R_5$ and $L$, respectively, or represent groups convertible thereto, $Q_1$ represents —CO— or —CHOH— or a group convertible thereto, and $R_{10}$ and $R_{12}$ each represent hydrogen or a protecting group such as benzyl, or a salt thereof with a compound of the formula III

wherein $R''''$ has the same meaning as R or represents a group convertible thereto, $X_1$ represents a leaving group, $Q'$ has the same meaning as Q or represents —CS—, or b. for the preparation of compounds wherein Q represents —CH$_2$—, reacting a compound of the above-mentioned formula II and wherein $R_{10}$ represents hydrogen, or a salt thereof with a compound of the formula IV

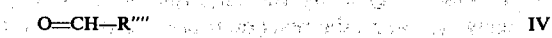

wherein $R''''$ has the above-mentioned meanings, or (when $R''''$ contains a basic group) a salt thereof, under reductive conditions, or c. reacting a compound of the formula V

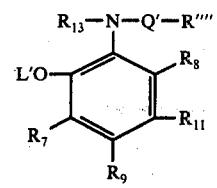

wherein $R''''$, $R_7$, $R_8$, $R_9$, $Q'$, and $L'$ each have the above-mentioned meanings, $R_{13}$ represents hydrogen or a protecting group such as benzyl in case $Q'$ represents —CO— or —CS— or represents a protecting group such as formyl or benzyloxycarbonyl in case $Q'$ represents —CH$_2$—, and $R_{11}$ represents a group of the formula

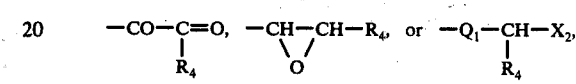

wherein $R_4$ and $Q_1$ each have the above-mentioned meanings, and $X_2$ represents a leaving group, with an amine of the formula VI

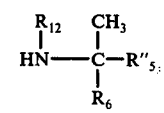

wherein $R''_5$, $R_6$, and $R_{12}$ each have the above-mentioned meanings, or a salt thereof, or d. reducing a compound of the formula VII

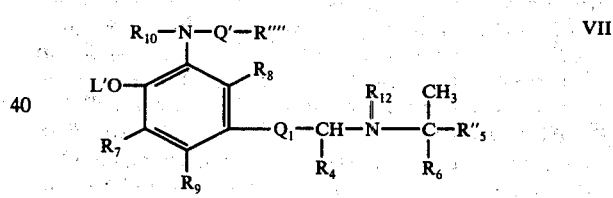

wherein $R''''$, $R_4$, $R''_5$, $R_6$, $R_7$, $R_8$, $R_9$, $R_{10}$, $R_{12}$, $Q'$, $Q_1$ and $L'$ each have the above-mentioned meanings, with the proviso that $Q'$ represents a thiocarbonyl or carbonyl group and/or that $Q_1$ represents a carbonyl group, or a salt thereof, or e. for the preparation of compounds wherein Q represents —CH$_2$—, reducing a compound of the formula VIII

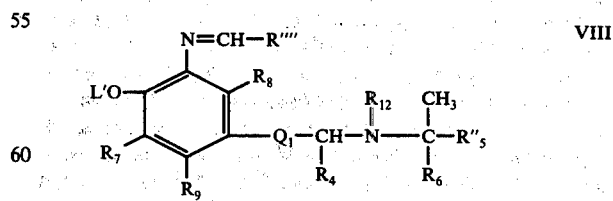

wherein $R''''$, $R_4$, $R''_5$, $R_6$, $R_7$, $R_8$, $R_9$, $R_{12}$, $L'$, and $Q_1$ each have the above-mentioned meanings, or a salt thereof, or f. for the preparation of compounds wherein $R_7$ is halogen, halogenating a compound of the formula IX

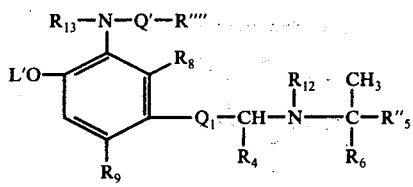

wherein R'''', R$_4$, R''$_5$, R$_6$, R$_8$, R$_9$, R$_{12}$, R$_{13}$, L', Q', and Q$_1$ each have the above-mentioned meanings, or a salt thereof, or g. reacting a compound of the formula X

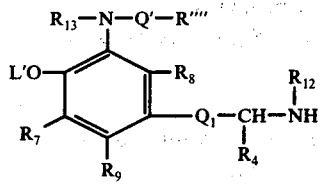

wherein R'''', R$_4$, R$_7$, R$_8$, R$_9$, R$_{12}$, R$_{13}$, Q', and Q$_1$ each have the above-mentioned meanings, or a salt thereof with a compound of the formula XI

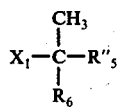

wherein R''$_5$, R$_6$, and X$_1$ each have the above-mentioned meanings, or (when R''$_5$ contains a basic group) a salt thereof, and, if necessary, subsequently to any of the reactions a) –g) converting one or more of the groups or moieties R'''', R''$_5$, L', Q', and Q$_1$, respectively, into the corresponding groups or moieties R, R$_5$, L, Q, and —CHOH—, respectively, and/or, if necessary, splitting off a protecting group R$_{12}$, R$_{13}$, and/or R$_{10}$, and/or, if desired, converting one or more of the radicals R, R$_5$, R$_7$, and L into other radicals within the definition of R, R$_5$, R$_7$, and L, and, if desired, converting a compound of the formula I obtained as the free base into a salt thereof, or, if desired, converting a compound of the formula I obtained as a salt thereof into the free base or into another salt thereof.

As examples of salts of the above-mentioned compounds may be mentioned acid addition salts with inorganic or organic acids such as hydrochloric, sulfuric, phosphoric, acetic, maleic, oxalic citric, fumaric, tartaric, ascorbic, succinic, and p-toluenesulfonic acid, which salts may be prepared by procedures known per se, e.g. by adding the acid in question to the base, preferably in a solvent. When more than one basic amino function are present, either one or more thereof may form salt. When e.g. Q is —CH$_2$—, such as in the above-mentioned preferred compound, 3-(4-methoxybenzylamino)-4-hydroxy-α-(tert.butylaminomethyl)benzylalcohol, a mono-salt or a di-salt may be prepared, e.g. with the above-mentioned inorganic or organic acids. The term "group convertible thereto" as used herein designates e.g. the corresponding groups containing protected groups such as protected hydroxy and amino groups or protecting groups for hydroxy or amino groups; groups convertible into such groups are known, and the introduction of said groups in the above-mentioned starting compounds and the subsequent conversion of said groups into the desired groups are carried out by methods known per se. As examples of protecting groups for hydroxy and amino groups may be mentioned benzyl, aromatically or aliphatically substituted benzyl such as diphenylmethyl or p-methoxybenzyl, alkoxycarbonyl such as tert.butoxycarbonyl or benzyloxycarbonyl, or aryloxycarbonyl such as p-nitrophenoxycarbonyl. Most of these protecting groups may be removed by hydrogenolysis with noble metal catalysts, preferably e.g. palladium on charcoal at a low temperature; however, in case sulfur is present in the compound in question it is desirable to use a modified catalyst. As an example of a protecting group which is removed in another way may be mentioned tert.butoxycarbonyl which may be removed by hydrolysis, e.g. with cold hydrochloric acid in argon. A further example of a protecting group is trimethylsilyl which may be removed by hydrolysis, e.g. with water. The term "group convertible thereto" also comprises cases wherein two groups, e.g. two of the above-mentioned groups, together are protected, and as examples of such protected groups may be mentioned two protected hydroxy groups such as —O—CO—O— (cyclic carbonate).

The group R$_{10}$ is preferably hydrogen. As examples of protecting groups R$_{10}$, benzyl may be mentioned in case the moiety Q' is, e.g., a carbonyl group, or R$_{10}$ may be formyl or benxyloxycarbonyl in a compound of the formula VII wherein Q' is, e.g., methylene.

The reaction of a compound of the formula II or a salt thereof with a compound of the formula III according to process variant a) is in principle an N-alkylation, an N-acylation, or an N-thioacylation which may be performed in a manner known per se. The compound of the formula III is e.g. a halide, an activated ester, an acid anhydride, a mixed anhydride, or an onium salt wherein X$_1$, e.g., represents halogen or (when Q' represents —CH$_2$—) substituted sulfonyloxy, or a charged hetero atom, or (when Q' represents —CO—) hydroxy, mercapto, substituted sulfonyloxy, substituted carbonyloxy, substituted carbonylthio, activated alkoxy, or alkylthio, or (when Q' represents —CS—) hydroxy, mercapto, substituted carbonyloxy, alkoxy, or alkylthio.

As preferred examples of groups X$_1$ may be mentioned the following: halogen is, e.g., bromine or preferably chlorine; substituted sulfonyloxy is, e.g., p-toluenesulfonyloxy or benzensulfonyloxy; a charged hetero atom is, e.g., the residue of an "onium compound", e.g. of an ammonium (X$_1$ = e.g. trimethylamine) or a sulfonium salt (X$_1$ = e.g. dimethylsulfide); substituted carbonyloxy is, e.g., the residue of an acid anhydride, e.g. ethoxycarbonyloxy or benzyloxycabonyloxy, activated alkoxy is, e.g., cyanomethoxy or polyhalogenated alkoxy such as 2,2,2-trifluoroethoxy; substituted carbonylthio is, e.g., the residue of a thioanhydride wherein X$_1$ preferably is a group of the formula —S—CO—R'''' wherein R'''' has the above-mentioned meaning; alkylthio is, e.g., methylthio, ethylthio or carboxymethylthio; and alkoxy is, e.g., methoxy or ethoxy.

When it is desired to prepare compounds wherein Q represents —CO—, by the N-acylation according to process variant a), the reaction is preferably carried out by adding a compound of the formula III, wherein X$_1$ preferably is a halide such as bromine or preferably chlorine, or X$_1$ is alkoxycarbonyloxy, which compound may be dissolved in e.g. acetone, to a solution of a compound of the formula II or a salt thereof, preferably the hydrochloride, in e.g. water or a mixture of water and acetone. The reaction is normally exothermic, and it is often desired to cool the mixture. The reaction is preferably performed at a temperature about room temperature or below, although somewhat higher temperatures may also be suitable in some cases, preferably below 30° C. The yield may be increased by the addition of an acid acceptor such as pyridine. The reaction time may vary between some minutes and several days; for practical reasons, the reaction on a laboratory scale is normally finished after one day and night. In case the resulting product is insoluble in the solvent used, it can be filtered off; otherwise, the resulting product may be recovered by evaporation of the solvent. Instead of mixtures of water and acetone, any other suitable solvent or solvent mixture inert to the reactants and reaction products may be used. In case $X_1$ represents, e.g. hydroxy it is desirable to add a condensing agent such as a carbodiimide, e.g. dicyclohexylcarbodiimide, and to carry out the reaction in an inert solvent such as pyridine.

When it is desired to prepare compounds wherein Q represents —$CH_2$—, by the N-alkylation according to process variant a), the reaction may be carried out analogously to the above-mentioned N-acylation according to process variant a), with the proviso that it can be desirable to heat the mixture of a compound of the formula II or a salt thereof and a compound of the formula III.

When it is desired to prepare compounds wherein Q' represents —CS—, by the N-thioacylation according to process variant a), the reaction may be carried out analogously to the above-mentioned N-acylation according to process variant a).

It has surprisingly been found that process variants a) and b) can be performed without any protecting group in the starting compounds, e.g. using as starting compound a salt, such as the hydrochloride, of a compound of the formula II wherein L' is hydrogen, and $Q_1$ represents —CHOH—, and $R_{12}$ represents hydrogen.

The reaction of a compound of the formula II or a salt thereof with a compound of the formula IV or a salt thereof according to process variant b) is in principle a reductive N-alkylation which may be performed in a manner known per se. The reductive conditions are preferably established by use of hydrogen in the presence of a catalyst. The hydrogenation is preferably carried out by mixing the two reactants in a solvent such as an alcohol, e.g. methanol, with a catalyst, e.g., $PtO_2$ or platinum on charcoal may be added, and by introducing a current of hydrogen into the mixture, suitably with agitation. The hydrogenation may be conducted at normal pressure and may be completed within 0.5 - 10 hours. When the uptake of hydrogen is finished, the catalyst may be removed by filtration, and the resulting product may be recovered by evaporation of the solvent in an inert atmosphere such as argon. When $R_{12}$ is a protecting group, it may be split off during the reaction or subsequently to the reaction. For example, a benzyl group $R_{12}$ may be split off using $Pd/H_2$.

Process variant c) is in principle an N-alkylation which may be performed in a manner known per se.

When using a starting compound of the formula V wherein $R_{11}$ is a group of the formula

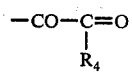

wherein $R_4$ has the above-mentioned meanings, it is especially preferred that $R_{12}$ in the compound of the formula VI represents hydrogen, and the reaction may be carried out in an inert solvent such as ethanol or diluted ethanol and by the addition of a reducing agent such as sodium borohydride for reduction of the intermediate formed in situ. The process is preferably carried out at room temperature, but higher or lower temperatures may be used.

When using a starting compound of the formula V wherein $R_{11}$ is a group of the formula

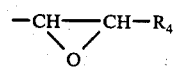

wherein $R_4$ has the above-mentioned meanings, the reaction may be carried out in an inert solvent, preferably an alcohol which is able to dissolve the starting compounds and which preferably has a sufficiently low boiling point to avoid decomposition of reactants and/or reaction products, e.g. methanol or ethanol. The reaction is preferably carried out in a short period of time, e.g. 1 hour, with reflux in an inert atmosphere such as argon.

When using a starting compound of the formula V wherein $R_{11}$ is a group of the formula

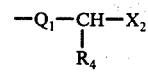

wherein $R_4$, $X_2$, and $Q_1$ each have the above-mentioned meanings, it is especially preferred that $X_2$ is halogen such as bromine, and that $R_{12}$ in the compound of the formula VI represents a protecting group, e.g. benzyl.

The reaction may be carried out in an inert solvent, e.g. acetonitrile or benzene, and the reaction temperature is preferably room temperature, but higher or lower temperatures may be used.

As examples of leaving groups $X_2$ may be mentioned halogen, substituted sulfonyloxy, or a charged hetero atom, and specific examples thereof are stated above.

When $R_{13}$ is a protecting group, this may be split off in a manner known per se. For example benzyl may be split off by catalytic hydrogenation, trichloroethoxy may be split off using zinc powder in diluted acetic acid, benzyloxycarbonyl may be split off using hydrobromic acid in glacial acetic acid at room temperature, and formyl may be split off using 1N hydrochlorid acid in methanol.

When $R_{12}$ is a protecting group, this may be split off during the reaction or subsequently to the reaction. For example, a benzyl group $R_{12}$ may be split off using $Pd/H_2$.

The reduction of a compound of the formula VII or a salt thereof according to process variant d) may be performed in a manner known per se. The reduction of a carbonyl group $Q_1$ to form a group of the formula —CHOH— may be performed with sodium borohydride or complex metal hydrides; for example lithium aluminum hydride may be used in case the compound of the formula VI is soluble in the solvent used for the dissolution of the lithium aluminum hydride, e.g. ether or tetrahydrofuran. Alternatively, the reduction may be performed by catalytic hydrogenation using, e.g., a noble metal catalyst such as palladium on charcoal, preferably platinum oxide or platinum on charcoal. The reduction is preferably carried out at room temperature but higher or lower temperatures may be used. The reduction of a thiocarbonyl group Q' into a methylene group may be performed using a hydrogen-saturated nickel cartalyst. The reduction can be performed in an inert solvent which is able to dissolve the starting compound, which does not react with the starting compound or the desired product, and which can be easily removed; as an example of such a solvent may be mentioned methanol.

The reduction of a compound of the formula VIII or a salt thereof according to process variant e) may be performed in a manner known per se, e.g. using sodium borohydride, or preferably catalytically using a catalyst such as Raney nickel, platinum oxide, or platinum on charcoal, and the reaction is preferably carried out in an inert solvent such as an alcohol, e.g. ethanol, or diluted ethanol may be the solvent in case sodium boro hydride is used, or methanol may be the solvent in case the reduction is performed catalytically. The reduction is preferably carried out at room temperature, but higher or lower temperatures may be used. When $R_{12}$ is a protecting group, this may be split off during the reaction or subsequently to the reaction. For example, a benzyl group $R_{12}$ may be split off using $Pd/H_2$.

The introduction of a halogen atom $R_7$ according to process variant f) may be performed in a manner known per se; for example, a chlorine atom $R_7$ may be introduced in the benzene ring by treating the starting compound with gaseous chlorine (or a chlorine solution), preferably in an inert solvent such as glacial acetic acid. The reaction temperature is preferably room temperature, but higher or lower temperatures may be used.

The reaction of a compound of the formula X with a compound of the formula XI according to prosess variant g) is in principle an N-alkylation which may be performed in a manner known per se, e.g. as stated above in connection with the N-alkylation according to process variant a).

After performing some of the above-mentioned process variants it may be necessary to convert one or more groups or moieties stated by the symbols $R''''$, $R'''_5$, $L'$, $Q'$, and $Q_1$, respectively, into the corresponding groups or moieties R, $R_5$, L, Q, and -CHOH-, respectively, to obtain a compound of the formula I or a salt thereof. As examples of such necessary conversions may be mentioned the conversion of a benzyloxy group present in $R''''$ into the corresponding free hydroxy group, and the conversion of a protected hydroxy group present in $Q_1$ into the corresponding free hydroxy group.

Another example of a necessary conversion to be carried out after some of the main reactions is the conversion of a thiocarbonyl group Q' into a carbonyl group, which may be performed as known per se, e.g. using silver oxide. Further examples of a necessary conversion to be carried out after some of the main reactions is the reduction of a carbonyl group $Q_i$ into a group of the formula —CHOH—, the reduction of a thiocarbonyl group Q', into a methylene group (both of which conversions are explained in greater detail above), and the removal of any protecting group $R_{10}$, $R_{12}$, and/or $R_{13}$ (e.g. the removal of a benzyl group using $Pd/H_2$). In a compound obtained by one of the above-mentioned process variants, e.g. a compound of the formula I or a salt thereof, it may be desired to convert some of the radicals R, $R_5$, and L into other radicals within the definition of R, $R_5$, and L. These conversions may be performed in manners known per se, and as example of such conversions may be mentioned that a nitro group $R_1$ - $R_3$ present in R may be hydrogenated to form an amino group $R_1$ - $R_3$ present in R.

It is within the knowledge of the skilled art worker to judge which groups should be protected in the starting compounds during the performance of the above-mentioned processes. As an example of a reaction in which a protecting group is used may be mentioned the preparation of compounds of the formula I wherein an amino group is present in R, by process variant a), in which case the amino group present in $R''''$ has to be protected, e.g. by a benzyloxycarbonyl group. It is to be understood that the term "protecting groups" also covers such protecting groups which are removed during the reaction, and, of course, the protecting group in each particular case should be so selected that it does not to any substantial degree adversely influence the reaction.

Compounds of the formula II are known or analogues to known compounds and may be prepared in a known manner or in analogy with known methods. One method to prepare compounds II wherein $R_4$ is hydrogen, is shown in the following scheme:

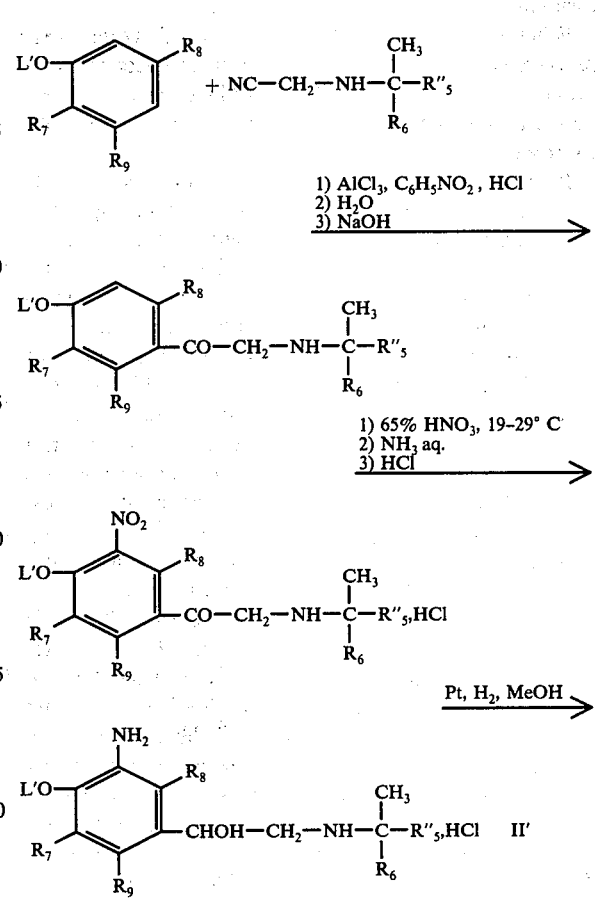

wherein $R''_5$, $R_6$, $R_7$, $R_8$, $R_9$, and $L'$ each have the above-mentioned meanings. In this synthesis, $L'$ is preferably hydrogen in the processes to be carried out before the above-stated nitration.

One method to prepare compounds of the formula II wherein $R_4$ is hydrogen or lower alkyl, is shown in the following scheme:

known processes. One method to prepare compounds of the formula V is shown in the following scheme:

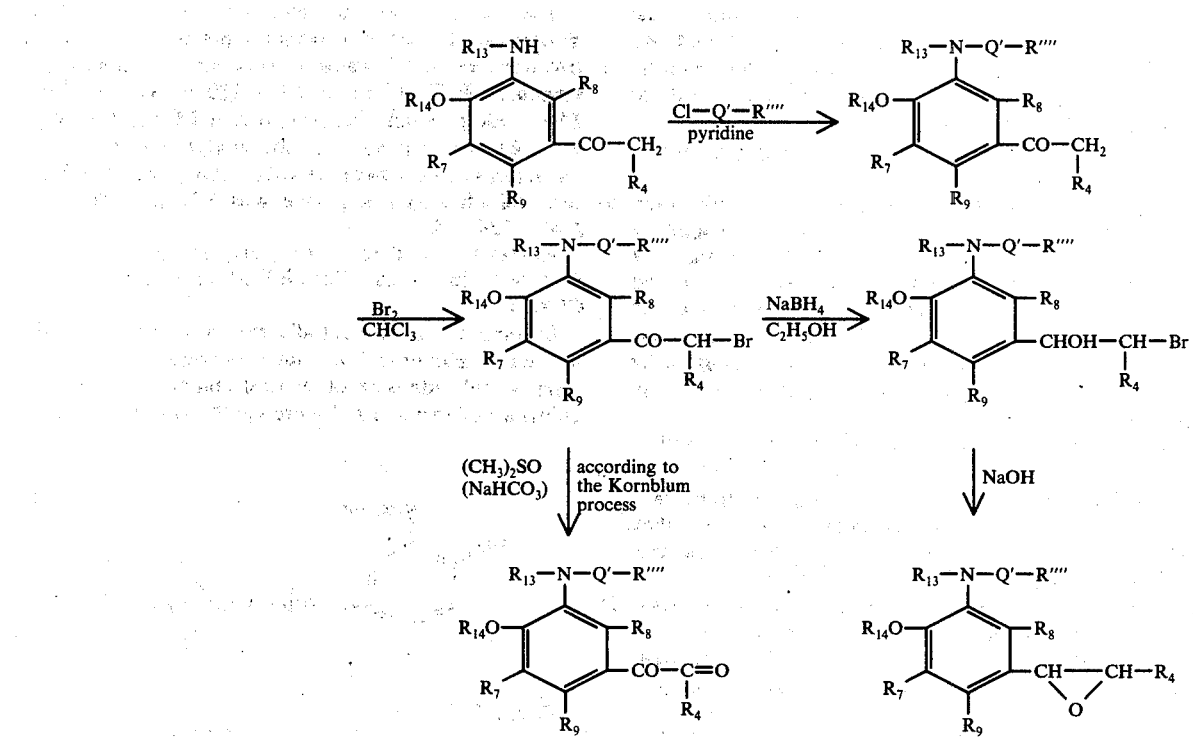

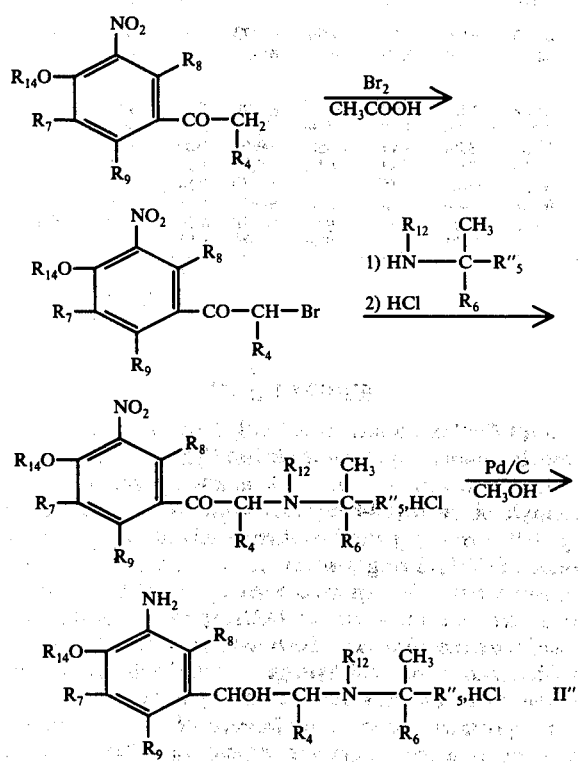

wherein $R_4$, $R''_5$, $R_6$, $R_7$, $R_8$, $R_9$, and $R_{12}$ each have the above-mentioned meanings, and $R_{14}$ represents a protecting group (e.g. benzyl) (or has the same meaning as L' with the proviso that $R_{14}$ is different from hydrogen).

Compounds of the formula V and salts thereof may be prepared in a known manner or in analogy with wherein $R''''$, $R_4$, $R_7$, $R_8$, $R_9$, $R_{13}$, $R_{14}$, and $Q'$ each have the above-mentioned meanings. When preparing compounds of the general formula V wherein $Q'$ represents —$CH_2$—, $R_{13}$ is, e.g., trichloroethoxycarbonyl, benzyloxycarbonyl, or preferably formyl.

Compounds of the formula VIII are formed as intermediates by process variant b) and may in some cases be isolated in process variant b).

Those starting materials, for which the preparation is not described herein, are either known compounds or compounds which may be prepared by analogy with the preparation of known compounds or in analogy with known processes.

A compound prepared by any of the above-mentioned processes may be isolated and purified in a manner known per se, e.g. by filtration, evaporation of the solvent, and recrystallization.

The process according to the present invention is further illustrated by the following examples which, however, are not to be construed as limiting. The examples especially illustrate the preferred embodiments of the process. Furthermore, the preparation of the starting compounds is illustrated in the examples.

EXAMPLE 1

3-(4-Nitrobenzamide)-4-hydroxy-α-(tert-butylaminomethyl)benzylalcohol hydrochloride.

(a) 4-Hydroxy-ω-(N-tert.butylamino)acetophenone.

This compound was prepared by the method of H. D. Moed et al., Rec. Trav. Chim. Pays-Bas 71, 933 (1952).

(b) 3-Nitro-4-hydroxy-ω-(tert.butylamino)acetophenone nitrate.

4-Hydroxy-ω-(tert.butylamino)acetophenone (394 g, 1.9 moles) was added to 65% nitric acid (1.6 liters) with stirring during 1 hour at 17° – 28° C (ice bath used occasionally). The clear dark solution, which towards the end of the addition became turbid, was kept for 1 hour with stirring at room temperature, whereafter water (1.2 liters) was added with cooling in an ice bath to 15° – 25° C. After standing for further 1 hour in the ice bath, the separated yellow solid was filtered off, washed with water, and air-dried. The yield of 3-nitro-4-hydroxy-ω-(tert.butylamino)acetophenone nitrate was 500 g (84%), m.p. 158° – 161.2° C.

(c) 3-Nitro-4-hydroxy-ω-(tert.butylamino)acetophenone hydrochloride.

3-Nitro-4-hydroxy-ω-(tert.butylamino)acetophenone nitrate (247 g, 0.79 mole) was suspended in 1N aqueous ammonia (1.6 liters) and stirred at room temperature for 4 hours. The separated yellow substance was filtered off, washed with water (600 ml), suspended in water (3.4 liters) and stirred for 1 hour. The substance was filtered off, air-dried, and finally dried in vacuum over sulphuric acid. The yield of the free base was 211 g, m.p. 146° – 148° C.

The free base was dissolved in a mixture of 3N hydrochloric acid (420 ml) and water (1680 ml) by heating to the boiling point and the faintly turbid solution was filtered. By cooling and scratching a yellow crystalline substance separated, and after standing at 5° C the substance was filtered off, air-dried, and dried over sulphuric acid in vacuum. The yield of 3-nitro-4-hydroxy-ω-(tert.butylamino)acetophenone hydrochloride was 197 g (86%), m.p. 214.8° – 217° C. (d) 3-Amino-4-hydroxy-α-(tert.butylaminomethyl)benzylalcohol hydrochloride.

A mixture of 3-nitro-4-hydroxy-ω-(tert.butylamino)acetophenone hydrochloride (10 g, 0.035 mole), methanol (250 ml), and PtO₂ (250 mg) was placed in a hydrogenation apparatus and hydrogenated using a hydrogen pressure of 2 atm. After 17 hours, the calculated amount of hydrogen had been absorbed, and the filtrate was evaporated in vacuum at 40° – 50° C. The residue was a yellow foam. The analogous procedure was carried out a further three times using the same amount of starting materials. To the combined foamy residues (34 g) ethanol (90 ml) (temperature 50° C) was added. By scratching, the foam was converted into a crystalline substance which, after standing at −20° C, was filtered off, washed with ether, and air-dried. The yield of 3-amino-4-hydroxy-α-(tert.butylaminomethyl)-benzylalcohol hydrochloride was 27.5 g (75%), m.p. 199° – 200° C.

(e) 3-(4-Nitrobenzamido)-4-hydroxy-α-(tert.butylaminomethylbenzylalcohol hydrochloride.

To a solution of 3-amino-4-hydroxy-α-(tert.butylaminomethyl)benzylalcohol hydrochloride (5.2 g, 0.02 mole) in water (10 ml) and acetone (70 ml) was added with stirring p-nitrobenzoyl chloride (3.7 g, 0.02 mole) in one portion. The temperature rose to 27° C in 2 minutes and a yellow substance precipitated. After standing for 24 hours at room temperature, the precipitate was filtered off, washed with ether, and air-dried. A substance (6.87 g), m.p. 218.2° – 220° C, was obtained. The crude product was recrystallized from 70% ethanol (164 ml). The yield of the analytically pure 3-(4-nitrobenzamido)-4-hydroxy-α-(tert.butylaminomethyl)-benzylalcohol hydrochloride was 5.32 g (65%), m.p. 234° – 234.2° C.

Analysis: Calculated for $C_{19}H_{24}ClN_3O_5$: C 55.67; H 5.90; N 10.25; Cl 8.65; Found: C 55.90; H 6.02; N 10.38; Cl 8.75.

By employing substantially the same method as described in Example 1 e), but substituting the p-nitrobenzoyl chloride with other acid chlorides, the hydrochlorides of formula I'''' were synthesized (Table 1)

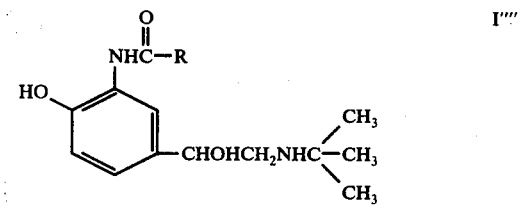

Table 1

| Example No. | R | m.p. °C | Calculated %C | %H | %N | %Cl | Found %C | %H | %N | %Cl |
|---|---|---|---|---|---|---|---|---|---|---|
| 2 | 3-nitrophenyl | 231.6–232 | 55.67 | 5.90 | 10.25 | 8.65 | 55.45 | 5.85 | 10.08 | 8.53 |
| 3 | 2-nitrophenyl | 175.4–177.8* | 53.78 | 6.08 | 9.91 | 8.36 | 53.80 | 6.09 | 10.00 | 8.35 |
| 4 | 3,5-dinitrophenyl | 169.2–174 | | | | | | | | |
| 5 | 4-methoxyphenyl | 225.4–225.6 | 60.83 | 6.89 | 7.10 | 8.98 | 60.70 | 7.01 | 6.95 | 8.72 |
| 6 | 3-methoxyphenyl | 205–207 | 60.83 | 6.89 | 7.10 | 8.98 | 60.65 | 6.93 | 7.06 | 8.90 |
| 7 | 3,4-dimethoxyphenyl | 148–153 | | | | | | | | |
| 8 | 3,4,5-trimethoxyphenyl | 154.2–158.6 | | | | | | | | |
| 9 | 4-ethoxyphenyl | 222.2–222.8 | 61.68 | 7.15 | 6.85 | 8.67 | 61.50 | 7.25 | 6.75 | 8.50 |
| 10 | 4-chlorophenyl | 238–238.6 | 57.14 | 6.06 | 7.02 | 17.76 | 57.25 | 6.18 | 6.97 | 17.73 |
| 11 | 3,4-dichlorophenyl | 224.6–226.8 | 52.61 | 5.34 | 6.46 | 24.52 | 52.55 | 5.40 | 6.39 | 24.58 |
| 12 | 4-methylphenyl | 217–219 | 63.39 | 7.18 | 7.40 | 9.36 | 63.25 | 7.33 | 7.47 | 9.41 |
| 13 | 4-benzyloxyphenyl | 195–200 | 66.30 | 6.63 | 5.95 | 7.53 | 66.40 | 6.58 | 5.57 | 7.01 |
| 14 | 3,5-dibenzyloxyphenyl | 177–180 | 68.68 | 6.46 | 4.86 | 6.14 | 68.55 | 6.51 | 4.88 | 6.34 |
| 15 | 2-thienyl | 199.6–200 | 55.05 | 6.25 | 7.55 | 9.56 | 55.10 | 6.14 | 7.50 | 9.63 |
| 16 | 2-furyl | 204–205** | 54.76 | 6.75 | 7.52 | 9.51 | 54.85 | 6.93 | 7.35 | 9.33 |

*with 0.8 mole of water
**with 1 mole of water

EXAMPLE 17

3-(4-Methoxybenzylamino)-4-hydroxy-α-(tert.butylaminomethyl)-benzylalcohol hydrochloride.

A mixture of 3-amino-4-hydroxy-α-(tert.butylaminomethyl)-benzylalcohol hydrochloride (6.53 g, 0.025 mole), p-methoxybenzaldehyde (3.4 g, 0.025 mole), PtO₂ (180 mg), and methanol (125 ml) was placed in a hydrogenation apparatus and hydrogenated at normal pressure (20 – 30 cm H₂O superatmospheric) for one hour and 50 minutes. During this period of time, the calculated amount of hydrogen was absorbed, and the hydrogenation was interrupted by supplying argon. The platinum catalyst was filtered off with continued supply of argon, but in spite of this, the filtrate quickly became dark due to oxidation. The filtrate was immediately evaporated in vacuum at 40° – 50° C. The residue which was a light brown foam (9.53 g), was recrystallized twice by precipitation from ethanol/ether (1:1). The yield of the analytical pure 3-(4-methoxybenzylamino)-4-hydroxy-α-(tert.butylaminomethyl)benzylalcohol hydrochloride was 5.2 g (55%), m.p. 196.6° – 197.8° C.

Analysis: Calculated for $C_{20}H_{29}ClN_2O_3$: C 63.06; H 7.67; N 7.36; Cl 9.31; Found: C 63.10; H 7.80; N 7.35; Cl 9.41.

By employing substantially the same method as described in Example 17, but substituting the p-methoxybenzaldehyde with other aldehydes, the hydrochlorides of formula I'''' were synthesized (Table 2).

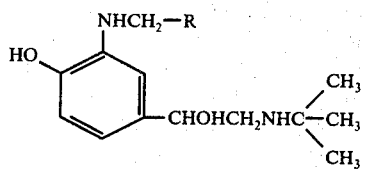

ethanol/ether analytically pure title compound, m.p. 190.4°–191.2° C was obtained.

Analysis: Calculated for $C_{19}H_{26}ClN_3O_3$: C 60.07; H 6.90; N 11.06; Cl 9.33; Found: C 59.95; H 6.98; N 11.01; Cl 9.27.

EXAMPLE 35

3-(4-Methoxybenzamido)-4-hydroxy-5-chloro-α-(tert.butylaminomethyl)benzylalcohol hydrochloride.

To a slurry of 3-(4-methoxybenzamido)-4-hydroxy-α-(tert.butylaminomethyl)benzylalcohol hydrochloride (0.5 g, 0.0013 mole) in glacial acetic acid (5 ml) a glacial acetic acid/chlorine solution (11.86 ml) containing 0.0898 g (0.0013 mole) of chlorine was added at room temperature with stirring during 10 minutes. The mix-

Table 2

| Example No. | R | m.p. ° C | Calculated | | | | Found | | | | Water of crystallization (mole/mole) |
|---|---|---|---|---|---|---|---|---|---|---|---|
| | | | %C | %H | %N | %Cl | %C | %H | %N | %Cl | |
| 18 | 4-Methylphenyl | 181.2–182 | 65.82 | 8.01 | 7.68 | 9.72 | 65.65 | 8.16 | 7.62 | 9.89 | |
| 19 | 4-Hydroxyphenyl | 187.4–188.6 | 61.29 | 7.47 | 7.53 | 9.53 | 61.32 | 7.49 | 7.51 | 9.65 | 0.3 |
| 20 | 3-Hydroxyphenyl | 183–184 | 60.13 | 7.54 | 7.38 | 9.34 | 60.20 | 7.58 | 7.36 | 9.20 | 0.7 |
| 21 | 2-Hydroxyphenyl | 148.8–150 | 59.85 | 7.56 | 7.35 | 9.30 | 59.70 | 7.53 | 7.33 | 9.14 | 0.8 |
| 22 | 3,4-Dimethoxyphenyl | 196–198 | 60.58 | 7.65 | 6.73 | 8.52 | 60.70 | 7.69 | 6.65 | 8.51 | 0.3 |
| 23 | 3,4,5-Trimethoxyphenyl | 108–112 | 57.93 | 8.02 | 5.75 | 7.28 | 57.90 | 7.76 | 5.79 | 7.28 | * |
| 24 | 4-Ethoxyphenyl | 202 | 63.86 | 7.91 | 7.09 | 8.98 | 63.70 | 7.88 | 7.05 | 8.92 | |
| 25 | 4-isoPropoxyphenyl | 202–203 | 64.61 | 8.13 | 6.85 | 8.67 | 64.55 | 8.02 | 6.77 | 8.73 | |
| 26 | 3-Methyl-4-hydroxyphenyl | 142–143 | 58.80 | 7.75 | 6.53 | 8.27 | 58.52 | 7.99 | 6.49 | 8.29 | ** |
| 27 | 3-Methyl-4-methoxyphenyl | 201.8–203.2 | 63.86 | 7.91 | 7.09 | 8.98 | 63.95 | 7.82 | 6.98 | 8.91 | |
| 28 | 3,5-Dimethyl-4-methoxyphenyl | 184.8–185.6 | 64.61 | 8.13 | 6.85 | 8.67 | 64.40 | 8.11 | 6.96 | 8.86 | |
| 29 | 4-(2-Methoxyethoxy)phenyl | 185.6–186.2 | 62.17 | 7.83 | 6.59 | 8.34 | 61.85 | 7.65 | 6.49 | 8.47 | |
| 30 | 4-(Carbamoylmethoxy)phenyl | 192.4–193.4 | 58.26 | 7.22 | 9.71 | 8.19 | 58.20 | 7.24 | 9.61 | 8.16 | 0.5 |
| 31 | 4-(Dimethylamino)phenyl | 188–189 | 63.44 | 8.21 | 10.57 | 8.92 | 63.15 | 8.22 | 10.42 | 9.20 | 0.2 |
| 32 | 2-Pyridyl | 179–181 | | | | | | | | | |

*Crystallized with 0.9 mole of water and 0.9 mole of methanol
**Crystallized with 1 mole of methanol

EXAMPLE 33

3-(4-Aminobenzamido)-4-hydroxy-α-(tert.butylaminomethyl)benzylalcohol hydrochloride.

A mixture of 3-(4-nitrobenzamido)-4-hydroxy-α-(tert.butylaminomethyl)benzylalcohol hydrochloride (7.37 g, 0.018 mole), $PtO_2$ (250 mg), and methanol (225 ml) was placed in a pressure hydrogenation apparatus at a starting pressure of 2 atm. The hydrogenation was started, and the calculated amount of hydrogen was taken up within 17 minutes. The hydrogenation was interrupted and the platinum catalyst was filtered off. The clear colorless filtrate was evaporated on a rotary evaporator at 40° – 50° C. The residue, a cream-colored foam (7.3 g), was recrystallized three times from methanol/ether, and 3.50 g (50%), m.p. 228.8° – 230° C, of analytically pure 3-(4-aminobenzamido)-4-hydroxy-α-(tert.butylaminomethyl)benzylalcohol hydrochloride, was obtained.

Analysis: Calculated for $C_{19}H_{26}ClN_3O_3$,0.4 $H_2O$: C 58.95; H 6.98; N 10.85; Cl 9.16; Found: C 58.90; H 7.06; N 10.72; Cl 8.93.

EXAMPLE 34

3-(2-Aminobenzamido)-4-hydroxy-α-(tert.butylaminomethyl)benzylalcohol hydrochloride.

In substantially the same manner as described above in Example 33 3-(2-nitrobenzamido)-4-hydroxy-α-(tert.butylaminomethyl) benzylalcohol hydrochloride was hydrogenated and after recrystallisation from ture was kept with continued stirring for 24 hours at room temperature, whereafter insoluble substance was filtered off, washed with ether, and air-dried (160 mg) (32%), melting point 196° – 199° C. 80 mg of the crude product was recrystallized from methanol (2 ml) (insoluble substance was filtered off). The yield of the analytically pure 3-(4-methoxybenzamido)-4-hydroxy-5-chloro-α-(tert.butylaminomethyl)benzylalcohol hydrochloride was 50 mg (20%), m.p. 205° – 206° C.

Analysis: Calculated for $C_{20}H_{26}Cl_2N_2O_4$: C 55.95; H 6.10; Cl 16.52; N 6.53; Found: C 56.00; H 6.13; Cl 16.79; N 6.46.

EXAMPLE 36

3-(4-Methoxybenzamido)-4-hydroxy-5-bromo-α-(tert.butylaminomethyl)benzylalcohol hydrobromide.

In substantially the same manner as described above in Example 35 3-(4-methoxybenzamido)-4-hydroxy-α-(tert.butylaminomethyl)benzylalcohol hydrobromide was brominated with bromine in glacial acetic acid. The analytically pure title compound was precipitated from the reaction mixture with ether. M.p. 168° – 169.6° C.

Analysis: Calculated for $C_{20}H_{26}Br_2N_2O_4$, $0.5H_2O$: C 45.55; H 5.13; N 5.35; Br 30.86; Found: C 45.55; H 5.16; N 5.31; Br 30.31.

EXAMPLE 37

3-(4-Hydroxybenzamido)-4-hydroxy-α-(tert.butylaminomethyl)-benzylalcohol hydrochloride.

3-(4-Benzyloxbenzamido)-4-hydroxy-α-(tert.butylaminomethyl)-benzylalcohol hydrochloride (4.71 g, 0.01 mole) (from Example 13), 10% Pd/C (450 mg), and methanol (150 ml) were mixed under argon atmosphere, and the mixture was placed in a hydrogenating apparatus and hydrogenated at normal pressure (20 – 30 cm $H_2O$ superatmospheric) for 30 minutes. During this period of time, 285 ml $H_2$ (theoretically 245 ml $H_2$ at 26° C) was absorbed. The hydrogenation was stopped by supplying argon. The Pd/C-catalyst was filtered off under argon atmosphere (danger of fire) and the colorless filtrate evaporated in vacuum at 40° – 50° C. The residue, a white foam (3.87 g), was recrystallized from ethanol/ether (3:5). The separated substance was dried in vacuum over $H_2SO_4$ to yield analytically pure 3-(4-hydroxy-benzamido)-4-hydroxy-α-(tert.butylaminomethyl)benzylalcohol hydrochloride (2.4 g) (63%), m.p. 210° C.

Analysis: Calculated for $C_{19}H_{25}ClN_2O_4$: C 59.91; H 6.62; Cl 9.31; N 7.36; Found: C 59.90; H 6.61; Cl 9.42; N 7.39.

EXAMPLE 38

3-(3,5-Dihydroxybenzamido)-4-hydroxy-α-(tert.butylaminomethyl)-benzylalcohol hydrochloride.

In substantially the same manner as described above in Example 37 3-(3,5-dibenzyloxybenzamido)-4-hydroxy-α-(tert.butylamino-methyl)benzylalcohol hydrochloride (Example 14) was hydrogenated and after recrystallisation from methanol/ether analytically pure title compound, m.p. 216°–218° C, was obtained.

Analysis: Calculated for $C_{19}H_{25}ClN_2O_5.0.3$ mole $H_2O$: C 56.73; H 6.41; Cl 8.81; N 6.97; Found: C 56.70; H 6.48; Cl 8.89; N 6.97.

EXAMPLE 39 a. 3-Nitro-4-benzyloxypropiophenone.

This compound was prepared by the method of A. A. Larsen et al., J. Med. Chem. 10, 462 (1967).

b. 3-Nitro-4-benzyloxy-α-bromopropiophenone.

To a 61° C warm solution of 3-nitro-4-benzyloxypropiophenone (91.3 g, 0.32 mole) in glacial acetic acid (830 ml), 12.5% of a solution containing bromine (51.1 g, 32 mole) in glacial acetic acid (420 ml) was added during 5 minutes with stirring. The yellow solution was cooled to 49° – 51° C, whereafter the remaining bromine solution was added during 30 minutes. After standing for a further 30 minutes at 49° – 51° C, the clear reddish brown solution was poured into ice-water (5 liters) with stirring. The separated brown greasy substance was extracted three times with chloroform (800 ml, 400 ml, and 400 ml, respectively). The combined chloroform extracts were washed three times with water (400 ml), and dried over magnesium sulphate. The chloroform was distilled off in vacuum, and the residue (118 g) was recrystallized from ethanol (350 ml). The yield of 3-nitro-4-benzyloxy-α-bromopropiophenone was 86.9 g (75%), m.p. 88.6° – 89.2° C.

From 3-Nitro-4-benzyloxy-α-bromopropiophenone the following compounds may be prepared:

c. 3-Nitro-4-benzyloxy-α-[N-benzyl-N-(tert.butyl)amino]propiophenone hydrochloride by reaction with N-benzyl-N-(tert.butyl)amine.

d. 3-Amino-4-benzyloxy-α-(1-[N-benzyl-N-(tert.butyl)amino]ethyl)-benzylalcohol hydrochloride from the nitro-keto compound (c) by reduction with $PtO_2$ and hydrogen by a method analogous to Example 1 d).

From 3-Amino-4-benzyloxy-α-(1-[N-benzyl-N-(tert.butyl)amino]ethyl)-benzylalcohol hydrochloride the following compounds may be prepared:

e. 3-(4-Methoxybenzamido)-4-hydroxy-α-[1-(tert.butylamino)ethyl]-benzylalcohol hydrochloride by N-acylation with p-methoxybenzoyl chloride analogously to the process described in Example 1 e), and thereafter converting the 4-benzyloxy group into 4-hydroxy and the N-benzyl-N-tert.butylamino group into a tert.butylamino group using $H_2$/Pd by a method analogous to Example 37.

f. 3-(4-Methoxybenzylamino)-4-hydroxy-α-[1-(tert.butylamino)ethyl]-benzylalcohol hydrochloride by N-alkylation with p-methoxybenzaldehyde analogous to the method described in Example 17, and thereafter converting the 4-benzyloxy group into 4-hydroxy and the N-benzyl-N-tert.butylamino group into the tert.butylamino group using $H_2$/Pd by a method analogous to Example 37.

EXAMPLE 40 a. 3-Nitro-4-benzyloxy-α-bromoacetophenone.

The title compound was synthesized by methods similar to those described in Examples 39 a) and 39 b).

b. 3-Nitro-4-benzyloxy-α-(bromomethyl)-benzylalcohol.

To a solution of sodium boronhydride (1.49 g) in 320 ml of ethanol cooled in an ice-bath (5° C) 3-nitro-4-benzyloxy-α-bromoacetophenone (52.5 g, 0.15 mole) was added in small portions. The reaction mixture was stirred at 5° C for 30 minutes after the addition was completed and then at room temperature for 24 hours. Hydrochloric acid (220 ml) was added dropwise and the mixture was stirred at room temperature for 20 hours. The mixture was evaporated in vacuum and water (200 ml) was added to the residue. Extraction with three portions of ether (200 ml, 100 ml, 100 ml) yielded after washing of the combined extracts with water, drying over magnesium sulphate, and evaporation of the ether 49.04 g of a brown sirup.

c. 3-Nitro-4-benzyloxystyrene oxide.

To a solution of the crude 3-nitro-4-benzyloxy-α-(bromomethyl)-benzylalcohol (48.6 g, 0.138 mole) in ether (300 ml) was added a 30% aqueous sodium hydroxide solution (300 ml). The mixture, which became dark orange, was kept for 1 hour with stirring at room temperature. Water (1000 ml) was added, and the mixture was extracted twice with ether (250 ml). The combined ether extracts were washed three times with water (100 ml), dried over magnesium sulphate, and evaporated in vacuum. The yield of 3-nitro-4-benzyloxystyrene oxide, an orange-colored oil, was 38.5 g (97%).

d. 3-Nitro-4-benzyloxy-α-(tert.butylaminomethyl)-benzylalcohol hydrochloride.

To a suspension of crude 3-nitro-4-benzyloxystyrene oxide (35.4 g, 0.13 mole) in ethanol (135 ml), tert.butylamine (10 g, 0.137 mole) dissolved in ethanol (50 ml) was added in one portion with stirring and reflux. The mixture was refluxed for a further 4 hours, and the clear red reaction mixture was evaporated in vacuum. To the residue, a reddish brown oil, was added 3N hydrochloric acid (200 ml) and methanol (800 ml). After shaking, the mixture was evaporated in vacuum, at last twice with methanol. The brown syrupy residue (43.1 g) was dissolved in ethyl acetate (130 ml) and kept (after seeding) at −20° C. The separated substance was filtered off, washed with ice-cold ethyl acetate (60 ml), and air-dried (14.84 g) (30%), m.p. 185.2° – 189° C. 1 g of the crude product was recrystallized three times from ethanol yielding 0.59 g of analytically pure 3-nitro-4-benzyloxy-α-(tert.butylaminomethyl)-benzylalcohol hydrochloride, m.p. 192°–193° C.

Analysis: Calculated for $C_{19}H_{25}ClN_2O_4$: C 59.91; H 6.62; Cl 9.31; N 7.36; Found: C 60.00; H 6.63; Cl 9.52; N 7.27.

e. 3-Amino-4-benzyloxy-α-(tert.butylaminomethyl)-benzylalcohol maleinate.

To $SnCl_2 2H_2O$ (1.87 g, 0.0078 mole) was added concentrated hydrochloric acid (6 ml). The turbid mixture was kept overnight with stirring, whereby it became clear. 3-Nitro-4-benzyloxy-α-(tert.butylaminomethyl)-benzylalcohol hydrochloride (1 g, 0.0026 mole) was added in one portion with stirring. After stirring for a few minutes water (6 ml) was added and the mixture wherein a sticky substance separated, was heated to 80° C for a short period of time, whereby most of the product dissolved. The mixture was kept for a further hour at 50° – 60° C with stirring and to the yellow solution a 30% sodium hydroxide solution (20 ml) was added with water cooling. The turbid mixture was extracted three times with ether (20 ml), and the light yellow ether extracts were washed four times with water (10 ml). The ether extracts were evaporated in vacuum after drying over magnesium sulphate.

To the residue, which was a yellowish-brown syrup, was added maleic acid (0.24 g), whereafter it was dissolved in methanol. The methanol solution was evaporated in vacuum. The residue was a brown sirup (0.87 g). 0.73 g of the crude product was recrystallized twice from acetonitrile and twice from ethanol to yield 0.22 g (30%) of analytically pure 3-amino-4-benzyloxy-α-(tert-.butylaminomethyl)benzylalcohol maleinate, 0.5 ml $H_2O$, m.p. 154°–158.6° C.

Analysis: Caculated for $C_{23}H_{30}N_2O_6, 0.5\ H_2O$: C 62.85; H 7.11; N 6.38; Found: C 62.95; H 6.82; N 6.30.

From 3-Amino-4-benzyloxy-α-(tert.butylaminomethyl)benzylalcohol hydrochloride the following compounds may be prepared:

f. 3-(4-Methoxybenzamido)-4-hydroxy-α-(tert-.butylaminomethyl)-benzylalcohol hydrochloride by N-acylation with p-methoxy-benzoyl chloride analogous to the process described in Example 1e), and thereafter converting the 4-benzyloxy group into a 4-hydroxy group using $H_2$/Pd by a method analogous to Example 37.

g. 3-(4-Methoxybenzylamino)-4-hydroxy-α-(tert-.butylaminomethyl)-benzylalcohol hydrochloride by N-alkylation with p-methoxy-benzaldehyde analogous to the method described in Example 17, and thereafter converting the 4-benzyloxy group into a 4-hydroxy group using $H_2$/Pd by a method analogous to Example 37.

EXAMPLE 41 a. 3-Nitro-4-benzyloxy-α-methylstyrene oxide.

The title compound was prepared by substantially the same methods as those described in Examples 40 a) to 40 c).

b. 3-Nitro-4-benzyloxy-α-[1-(isopropylamino)ethyl]-benzylalcohol hydrochloride.

A mixture of 3-nitro-4-benzyloxy-β-methylstyrene oxide (0.54 g, 0.0019 mole), 2-propylamine (0.22 g, 0.0037 mole), and ethanol (15 ml) was heated for 24 hours at 150° C in an autoclave. The reddish brown reaction mixture was evaporated in vacuum. To the residue, a brownish black sirup (0.61 g), was added 3N hydrochloric acid (10 ml) and methanol until the solution was clear. The solution was evaporated in vacuum.

The residue was a brown greasy crystalline substance (0.65 g). 0.59 g of the crude product was recrystallized once from acetonitrile (18 ml) and once from ethanol (3 ml), respectively, to yield 0.27 g (41%) of 3-nitro-4-benzylox-α-[1-(isopropylamino)ethyl]-benzylalcohol hydrochloride, m.p. 201.4° – 203.2° C.

c. 3-Amino-4-hydroxy-α-(1-[isopropylamino]ethyl)-benzlalcohol hydrochloride.

A mixture of 3-nitro-4-benzyloxy-α-(1-[isopropylamino]ethyl)benzylalcohol hydrochloride (2.75 g, 0.008 mole), 10% Pd/C (350 mg), and methanol (20 ml) was hydrogenated at normal pressure for 22 hours. The hydrogenation was stopped by supplying argon. The Pd/C was filtered off under argon, and ether (20 ml) was added to the yellow filtrate. The title compound (1.42 g, 68%, m.p. 204° –206° C), which separated was collected and washed with ether.

d. 3-(4-Methoxybenzylamino)-4-hydroxy-α-(1-[isopropylamino]ethyl)benzylalcohol hydrochloride. 3-Amino-4-hydroxy-α-(1-[isopropylamino]ethyl)benzylalcohol hydrochloride (1.3 g, 0.005 mole) was alkylated with p-methoxybenzaldehyde (0.68 g, 0.005 mole) by the method described in Example 17. Evaporation of the reaction mixture left a semi-solid residue which was dissolved in methanol (4.5 ml). Addition of ether (18 ml) precipitated 0.18 g of the starting compound. Evaporation of the filtrate yielded 1.14 g of an amorphous solid, which was identified as the title compound by NMR.

EXAMPLE 42

3-Methyl-4-hydroxy-5-(4-methoxybenzylamino)-α-(tert.butylaminomethyl)benzyalcohol hydrochloride.

a. 3-Methyl-4-hydroxy-ω-(N-tert.butylamino)-acetophenone.

The compound was prepared from o-cresol by the method described in Example 1 a). The yield was 75% and the m.p. 188.2°–191.0° C (from ethanol).

b. 3-Methyl-4-hydroxy-5-nitro-ω-(tert.butylamino)-acetophenone hydrochloride.

The compound was synthesized by methods similar to those described in Examples 1 b) and 1 c). M.p. >250° C (from dilute hydrochloric acid).

c. 3-Methyl-4-hydroxy-5-amino-α-(tert-.butylaminomethyl)benzylalcohol hydrochloride. Hydrogenation of the nitro compound by the method described in Example 1 d) yielded 97%, m.p. 196.2°–198.2° C, of the title compound.

d. 3-Methyl-4-hydroxy-5-(4-methoxybenzylamino)-α-(tert.butylaminomethyl)benzylalcohol hydrochloride.

The above mentioned amino compound was benzylated by substantially the same method as described in Example 17. The m.p. of the analytically pure title compound was 181°–183° C.

Analysis: Calculated for $C_{21}H_{31}ClN_2O_3$: C 63.86; H 7.91; N 7.09; Cl 8.98; Found: C 63.90; H 7.94; N 7.13; Cl 8.97.

EXAMPLE 43

3-(4-Methoxybenzamido)-4-hydroxy-α-(tert-.butylaminomethyl)-benzylalcohol hydrochloride.

A solution of 4-methoxybenzoic acid (0.76 g, 0.0050 mole) and of triethyl amino (0.70 ml, 0.0050 mole) in dry acetone (8 ml) was cooled to −15° C and ethyl chloroformate (0.54 g, 0.0050 mole) was added dropwise. The mixture was stirred 30 minutes at −15° C, and 30 minutes at 0° C, and then cooled to −15° C. A solution of 3-amino-4-hydroxy-α-(tert.butylaminomethyl)benzylalcohol hydrochloride in acetone (10 ml) and water (1.7 ml) was cooled to −15° C and added to the reaction mixture in one portion. The solution obtained was stirred at −15° C for 30 minutes, at 0° C for 30 minutes, and at room temperature for 1 hour. The solution was evaporated in vacuum and the residue was recrystallized from water yielding 1.02 g (52%), m.p. 224°–225° C of the title compound, identical to the compound prepared in Example 5.

EXAMPLE 44

3-(4-Nitrobenzylamino)-4-hydroxy-α-(tert.butylaminomethyl)-benzylalcohol hydrochloride.

To a mixture of 3-amino-4-hydroxy-α-(tert.butylaminomethyl)-benzylalcohol hydrochloride (1.04 g, 0.004 mole), pyridine (0.32 g, 0.004 mole), water (2 ml), and acetone (7 ml) p-nitrobenzyl chloride (0.69 g, 0.004 mole) dissolved in acetone (5 ml) was added with stirring and supplying of argon during 30 minutes at room temperature. Under continued supply of argon, the clear light brown mixture was kept for 24 hours with stirring at room temperature. The reaction mixture was evaporated in vacuum. The residue was a yellow greasy substance (1.98 g). 1.48 g of the substance was recrystallized once from water, once from acetonitrile, and once from methanol/ether to yield 0.67 g (57%) of analytically pure 3-(4-nitrobenzylamino)-4-hydroxy-α-(tert.butylaminomethyl)benzylalcohol hydrochloride, m.p. 134.2°–136.6° C.

Analysis: Calculated for $C_{19}H_{26}ClN_3O_4$: C 57.86; H 6.62; Cl 8.96; N 10.62; Found: C 57.40; H 6.68; Cl 8.93; N 10.52.

EXAMPLE 45 a. 2,5-Dimethyl-4-hydroxy-ω-(N-tert.butylamino)acetophenone.

The compound was prepared from 2,5-dimethylphenol by the method described in 1 a). The yield was 58% and the m.p. 201°–210° C.

b. 2,5-Dimethyl-3-nitro-4-hydroxy-ω-(tert.butylamino)acetophenon hydrochloride.

The compound was synthesized by methods similar to those described in Examples 1 b) and 1 c). M.p. 194°–198.5° C.

c. 2,5-Dimethyl-3-amino-4-hydroxy-α-(tert.butylaminomethyl)benzylalcohol hydrochloride.

Hydrogenation of the nitro compound by the method described in Example 1 d) yielded 69% of the title compound, m.p. 180°–183.5° C (from ethanol).

From 2,5-Dimethyl-3-amino-4-hydroxy-α-(tert.butylaminomethyl)benzylalcohol hydrochloride the following compounds may be prepared:

e. 2,5-Dimethyl-3-(4-methoxybenzamido)-4-hydroxy-α-(tert.butylaminomethyl)benzylalcohol hydrochloride by N-acylation with p-methoxybenzoyl chloride analogously to the process described in Example 1 e).

f. 2,5-Dimethyl-3-(4-methoxybenzylamino)-4-hydroxy-α-(tert.butylaminomethyl)benzylalcohol hydrochloride by N-alkylation with p-methoxybenzaldehyde analogously to the method described in Example 17.

EXAMPLE 46 a. 3-Nitro-4-acetoxyacetophenone.

3-Nitro-4hydroxyacetophenoneone was refluxed for 5 hours with acetic acid anhydride and the title compound, m.p. 60°–61° C, was obtained.

b. 3-Nitro-4-acetoxy-α-bromoacetophenone.

A solution of 3-nitro-4-acetoxyacetophenone (3.0 g, 0.014 mole) in glacial acetic acid (25 ml) was heated to 50° C and two drops of a solution of bromine (2.3 g, 0.014 mole) in glacial acetic acid (5 ml) were added. The reaction mixture was cooled to room temperature and the rest of the bromine solution was added over a period of 10 minutes. The mixture was stirred at room temperature for 30 minutes and poured into ice-water (100 g). Extraction with ether and evaporation of the ether in vacuum yielded 4.20 g of an oil, identified by NMR to be the title compound.

c. From 3-nitro-4-acetoxy-α-bromoacetophenone, 3-nitro-4-acetoxy-α-[N-benzyl-N-(tert.butyl)amino]-acetophenone hydrochloride may be prepared by reaction with N-benzyl-N-(tert.butyl)amine, and from this product, d. 3-amino-4-acetoxy-α-[N-benzyl-N-(tert.butyl)aminomethyl]-benzylalcohol hydrochloride may be prepared analogously to Example 39 d).

From 3-Amino-4-acetoxy-α-[N-benzyl-N-(tert.butyl)aminomethyl]benzylalcohol hydrochloride the following compounds may be prepared:

e. 3-(4-Methoxybenzamido)-4-acetoxy-α-(tert.butylaminomethyl)benzylalcohol hydrochloride by N-acylation with p-methoxybenzoyl chloride analogous to the process described in Example 1 e), and thereafter converting the N-benzyl-N-tert.butylamino group into a tert.butylamino group using $H_2$/Pd by a method analogous to Example 37.

f. 3-(4-Methoxybenzylamino)-4-acetoxy-α-(tert.butylaminomethyl)benzylalcohol hydrochloride by N-alkylation with p-methoxybenzaldehyde analogous to the method described in Example 17, and thereafter converting the N-benzyl-N-tert.butylamino group into a tert.butylamino group using $H_2$/Pd by a method analogous to Example 37.

EXAMPLE 47

3-(4-Methoxybenzylamino)-4-hydroxy-α-(tert.butylaminomethyl)benzylalcohol hydrochloride.

A mixture of 3-nitro-4-hydroxy-ω-(tert.butylamino)acetophenone hydrochloride (10.0 g, 0.035 mole), $PtO_2$ (100 mg), p-methoxybenzaldehyde (5.0 g, 0.037 mole), and methanol (100 ml) was hydrogenated using a hydrogen pressure of 2 atm. After 24 hours the hydrogenation was interrupted by supplying argon. The reaction mixture was filtered and the filtrate evaporated in vacuum.

The residue was recrystallized three times from ethanol/ether yielding 6.6 g (49%) of the title compound, m.p. 189°–190° C, with an IR-spectrum identical to the compound prepared in Example 17.

EXAMPLE 48 a. 3-Nitro-4-benzyloxy-α-([α,α-dimethylphenetylamino]methyl)benzylalcohol hydrochloride.

A mixture of 3-nitro-4-benzyloxystyrene oxide (Example 40 c)) (1.0 g, 0.0037 mole) and α,α-dimethylphenetylamin (0.55 g, 0.0037 mole) in ethanol (10 ml) was refluxed for 4 hours. The ethanol was evaporated in vacuum and the residue was dissolved in ethanolic hydrochloric acid. After evaporation in vacuum the yellow residue was boiled with ethyl acetate (20 ml) and cooled. the precipitate was collected and shown to be α,α-dimethylphenethylamine hydrochloride (0.34 g). The filtrate was evaporated in vacuum. The residue (1.43 g, 85%), a yellow oil, was identified as the title compound by NMR.

From 3-nitro-4-benzyloxy-α-[α,α-dimethylphenethylamino)methyl]benzylalcohol hydrochloride may be prepared:

b. 3-Amino-4-hydroxy-α-[(α,α-dimethylphenethylamino)methyl]benzylalcohol hydrochloride by a method similar to Example 41 c).

From 3-Amino-4-hydroxy-α[(α,α-dimethylphenethylamino)methyl]benzylalcohol hydrochloride may be prepared:

c. 3-(4-Methoxybenzylamino)-4-hydroxy-α-](α,α-dimethylphenethylamino)methyl]benzylalcohol hydrochloride by N-alkylation with p-methoxybenzaldehyde by a method analogous to Example 17.

PHARMACOLOGICAL DATA

A series of compounds of the invention was tested for bronchospasmolytic effect ($\beta_2$-stimulation) according to the well-known Konzett-Rossler technique (in anaesthetized guinea pig lungs; Konzett, H. and Rossler, R.: Versuchsanordnung zu Untersuchungen an der Bronkialmuskulatur, Arch. Exp. Path. Pharmakol. 195, 71–74 (1940)), and a number of the compounds showed significant activity as appears from the following table, which also contains data on the heart rate increasing effect ($\beta_1$-stimulation). Furthermore the acute toxicity in mice after intraveneous and oral administration is given.

An especially valuable feature of the present invention is that typical and preferred representative of the compounds of the invention show a high bronchial selectivity (ratio of bronchospasmolytic activity to heart rate increasing effect) as compared to existing well-known broncholytics. This appears from the table, where the heart rate increasing effect was estimated in pentobarbital anaesthetized mice and expressed as "ED 100", i.e. the dose giving an incrase in heart rate of 100 beats/min. The ratio, heart rate increasing dose ("ED 100") divided by bronchospasmolytic dose (ED 50), is a measure of the degree of selectivity of the bronchospasmolytic action. This ratio was calculated for a number of the compounds of the invention and for some of the most relevant compounds of reference.

As appears from the table, the degree of bronchoselective action in considerably higher than that of isoprenaline. Furthermore some of the compounds show the same and even a higher degree of selectivity than that of salbutamol the hitherto most selective bronchospasmolytic in the human clinic.

For one compound, 3-(4-methoxybenzylamino)-4-hydroxy-α-(tert.butylaminomethyl)benzylalcohol hydrochloride, the bronchoselectivity was compared with that of salbutamol in conscious guinea pigs. The effective bronchospasmolytic doses of the two compounds were determined using a pressurized aerosol of a 1% acetylcholine solution as the spasmogen according to the method of Wardell, J. Pharmacol Exp. Therap. 1974, 189, 167–184 and the heart rate was determined according to Farmer et al. (Br. J. Pharmac. Chemotherap. 1968, 32, 193–200. In these experimental set ups 3-(4-methoxybenzylamino)-4-hydroxy-α-(tert.butylaminomethyl)benzylalcohol hydrochloride proved 10 times more active than salbutamol as a broncholytic, whereas the heart rate stimulating effect was the same.

Thus, the results indicate that the compounds of the invention may be administered in effective bronchospasmolytic dosages with less cardiac side-effects than known bronchospasmolytics.

For a few of the compounds of the invention, the tremor-inducing activity ($\beta$-stimulation of the skeletal muscles) was determined in cats (in accordance with the technique of Bowman, W. C. and Nott, M. W.: Actions of some sympathomimetic bronchodilator and beta-adrenoceptor blocking drugs on contractions of the cat soleus muscle, Brit. J. Pharmac., 1970, 38, 37–49) and compared to the bronchospasmolytic activity in the same species. It was found that 3-(4-methoxybenzamido)-4-hydroxy-α-(tert.butylaminomethyl)benzylalcohol hydrochloride showed the same ratio between bronchospasmolytic dose and tremor-inducing dose as salbutamol, whereas 3-(4-methoxybenzylamino)-4-hydroxy-α-(tert.butylaminomethyl)benzylalcohol hydrochloride showed a better ratio than salbutamol.

Compounds of the present invention are well tolerated, as appears from the table. For one compound, 3-(4-methoxybenzylamino)-4-hydroxy-α-(tert.butylaminomethyl)benzylalcohol hydrochloride, an acute intraveneous and oral toxicity test as well as a two week tolerance test in dogs have proved its good tolerability. Furthermore a three month toxicity test in rate of this compound has shown no toxic reactions.

|  | LD 50 mice mg/kg | | $\beta_2$-stimulation lungs guinea pig ED 50 | | $\beta_1$-stimulation Increase in heart rate mice "ED 100" | Ratio "ED 100"/ ED 50 |
|---|---|---|---|---|---|---|
|  | i.v. | p.o. | i.v. μg/kg | i.d.** mg/kg | i.v. μg/kg |  |
| 3-(4-Nitrobenzamido)-4-hydroxy-α-(tert.butylaminomethyl)benzylalcohol hydrochloride | 40 | >2000 | 100 | 10 | >1000 | >10 |
| 3-(4-Methoxybenzamido)-4-hyroxy-α-(tert.butylaminomethyl)benzylalcohol hydrochloride | 80 | >2000 | 100 | 10 | >1000 | >10 |
| 3-(3-Nitrobenzamido)-4-hydroxy-α-(tert.butylaminomethyl)benzylalcohol hydrochloride | 60 | >2000 | 300 |  |  |  |
| 3-(4-Chlorobenzamido)-4-hydroxy-α-(tert.butylaminomethyl)benzylalcohol hydrochloride | 60 | >2000 | 500 |  |  |  |
| 3-(3,4-Dichlorobenzamido)-4-hydroxy-α-(tert.butylaminomethyl)benzylalcohol hydrochloride | 60 | >2000 | 100 |  |  |  |
| 3-(4-Methoxybenzylamino)-4-hydroxy-α-(tert.butylaminomethyl)benzylalcohol hydrochloride | 20 | 300 | 3 | 1 | 100 | 33 |
| 3-(4-Methylbenzylamino)-4-hydroxy-α-(tert.butylaminomethyl)benzylalcohol hydrochloride | 20 | 700 | 70 |  |  |  |
| 3-(4-Hydroxybenzylamino)-4-hydroxy-α-(tert.butylaminomethyl)benzyl- |  |  |  |  |  |  |

-continued

| | LD 50 mice mg/kg | | $\beta_2$-stimulation lungs guinea pig ED 50 | | $\beta_1$-stimulation Increase in heart rate mice "ED 100" | Ratio "ED 100"/ |
|---|---|---|---|---|---|---|
| | i.v. | p.o. | i.v. μg/kg | i.d.** mg/kg | i.v. μg/kg | ED 50 |
| alcohol hydrochloride | 20 | >2000 | 10 | 10 | 70 | 7 |
| 3-(3,4-Dimethoxybenzylamino)-4-hydroxy-α-(tert.butylaminomethyl)benzylalcohol hydrochloride | 20 | >2000 | 10 | 10 | 90 | 9 |
| 3-(3-Hydroxybenxylamine)-4-hydroxy-α-(tert.butylaminomethyl)-benzylalcohol hydrochloride | 20 | ≅2000 | 10 | 10 | 25 | 2.5 |
| 3-(3,5-Dihydroxybenzamido)-4-hydroxy-α-(tert.butylaminomethyl)-benzylalcohol hydrochloride | 20 | >2000 | 300 | 20 | | |
| 3-(4-Ethoxybenzylamino)-4-hydroxy-α-(tert.butylaminomethyl)benzyl-alcohol hydrochloride | 20 | 400 | 10 | 5 | 100 | 10 |
| 3-(3-Methoxy-4-hydroxybenzylamino)-4-hydroxy-α-(tert.butylaminomethyl)-benzylalcohol hydrochloride | 10-30 | >2000 | 20 | | 50 | 2.5 |
| 3-(4-Isopropoxybenzylamino)-4-hydroxy-α-(tert.butylaminomethyl)-benzylalcohol hydrochloride | 20 | 400 | 30 | | 100 | 3.3 |
| 3-(4-Dimethylaminobenzylamino)-4-hydroxy-α-(tert.butylaminomethyl)benzylalcohol hydrochloride | 20 | 700 | 20 | | ≅100 | ≅5 |
| 3-(4-Nitro-benzylamino)-4-hydroxy-α-(tert.butylaminomethyl)benzyl-alcohol hydrochloride | 60 | 400 | 10 | 0.5 | 100 | 10 |
| 3-[4-(2-Methoxyethoxy)benzylamino]-4-hydroxy-α-(tert.butylaminomethyl)-benzylalcohol hydrochloride | 20 | >1000 | 10 | 1 | 100 | 10 |
| 3-(4-Acetamidoxybenzylamino)-4-hydroxy-α-(tert.butylaminomethyl)benzylalcohol hydrochloride | 20 | >1000 | 10 | 10 | 100 | 10 |
| 3-(3,5-Dimethyl-4-methoxybenzylamino)-4-hydroxy-α-(tert.butylaminomethyl)benzylalcohol hydrochloride | 20 | 1500 | 30 | 3 | 300 | 10 |
| Isoprenaline | 70 | >2000 | 5 | | 0.3 | 0.06 |
| Orciprenaline | 80 | >2000 | 100 | | 10 | 0.1 |
| Soterenol | 60 | 750 | 20 | | 40 | 2 |
| Terbutaline | 40 | >2000 | 30 | 10 | 300 | 10 |
| Saloutamol | 50 | 2000 | 10 | 5 | 100 | 10 |

*All doses are expressed as the free base of the racemic compound
** i.d. = intraduodenally

What is claimed is:

1. A phenylethanolamine of the formula

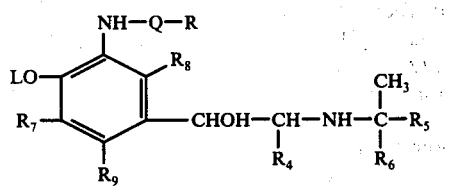

wherein R is a substituted phenyl group of the formula

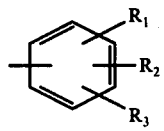

wherein $R_1$, $R_2$, and $R_3$ are the same or different and each represent hydrogen, hydroxy, halogen, trifluoromethyl, nitro, lower alkylcarbonyl, lower alkyl, lower alkoxy, hydroxy-lower alkyl, hydroxy-lower alkoxy, lower alkoxy-lower alkoxy, lower alkyl-carbonyl-lower alkoxy, or aryl-lower alkoxy, with the proviso that not all of $R_1$, $R_2$, and $R_3$ are hydrogen, $R_4$ is hydrogen or lower alkyl, $R_5$ is hydrogen, lower alkyl, or optionally substituted benzyl, and $R_6$ is hydrogen or lower alkyl, $R_7$ is hydrogen, halogen, or lower alkyl, $R_8$ is hydrogen or lower alkyl, $R_9$ is hydrogen or lower alkyl, Q is —CH$_2$—, and L is hydrogen and enantiomers and, when more than one asymmetric carbon atom is present, also diastereoisomers, and physiologically acceptable salts thereof.

2. A compound according to claim 1, wherein $R_1$ and $R_2$ are each hydrogen, $R_3$ is in the 4-position and is an alkoxy group or one of the substituted alkoxy groups defined in claim 1.

3. A compound according to claim 1, and having the formula I'

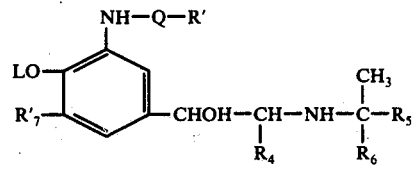

wherein $R_4$, $R_5$, $R_6$, L and Q are as defined in claim 1, R' is a substituted phenyl group of the formula

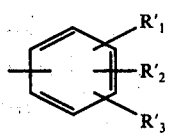

wherein $R'_1$, $R'_2$, and $R'_3$ are the same or different and each is hydrogen, nitro, hydroxy, lower alkoxy, or any of the substituted lower alkoxy groups set forth in the definition of $R_1$, $R_2$, and $R_3$ in claim 1, with the proviso that not all of R'$_1$, R'$_2$, and R'$_3$ are hydrogen and R'$_7$ is hydrogen, chlorine or bromine.

4. A compound according to claim 3, and having the formula I″

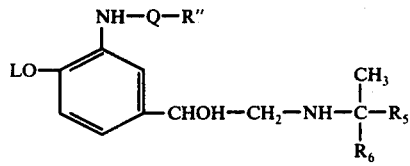

wherein Q, L, R$_5$ and R$_6$ are as defined, and R″ is 4-hydroxyphenyl, or a 4-alkoxyphenyl selected from the group consisting of 4-methoxyphenyl, 4-ethoxyphenyl, 4-isopropoxyphenyl and 4-tert.butoxyphenyl or 4-nitrophenyl.

5. A compound according to claim 3, wherein R$_4$ is hydrogen or methyl and when any of R'$_1$, R'$_2$ and R'$_3$ is alkoxy or substituted lower alkoxy, it is the only substituent on the phenyl group and is in the 4-position thereof.

6. A compound according to claim 1, and having the formula I‴

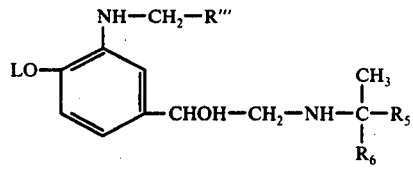

wherein R$_5$, R$_6$, and L are as defined in claim 1 and R‴ is 4-ethoxyphenyl, 4-methoxyphenyl, 4-hydroxyphenyl, 4-nitrophenyl, or 4-(2-methoxyethoxy)phenyl.

7. A compound according to claim 6, which is 3-(4-methoxybenzylamino)-4-hydroxy-α-(tert-.butylaminomethyl)benzyl-alcohol and physiologically acceptable salts thereof.

8. A compound according to claim 1, wherein R$_5$ and R$_6$ are each methyl.

9. A pharmaceutical composition comprising a bronchospasmolytically effective amount of a compound of the formula I as defined in claim 1 or a salt thereof together with a pharmaceutically acceptable carrier.

10. A pharmaceutical composition comprising a bronchospasmolytically effective amount of 3-(4-methoxybenzylamino)-4-hydroxy-α-(tert.butylaminomethyl)-benzylalcohol or a salt thereof together with a pharmaceutically acceptable carrier.

* * * * *

UNITED STATES PATENT OFFICE
CERTIFICATE OF CORRECTION

Patent No. 4,072,760              Dated February 7, 1978

Inventor(s) Kurt Hedegaard

It is certified that error appears in the above-identified patent and that said Letters Patent are hereby corrected as shown below:

Column 5, line 44: "α:(tert.butylaminomethyl)benzylalcohol," should read -- α-(tert.butylaminomethyl)benzylalcohol --.

Column 6, line 25: "3-[4-cyanomethoxy)benzylamino]-" should read -- 3-[4-(cyanomethoxy)benzylamino]- --; line 42: ".butylaminomethy)benzylalcohol," should read -- .butylaminomethyl)-benzylalcohol, --.

Column 9, line 11: "yl-2-]4-methoxyphenyl]ethylaminomethyl)-ben-" should read -- yl-2-[4-methoxyphenyl]ethylaminomethyl)-ben- --.

Column 12, line 28: "benxyloxycarbonyl" should read -- benzyloxycarbonyl --; lines 52-53: "benzyloxycabonyloxy" should read -- benzyloxycarbonyloxy --.

Column 14, line 64: "agroup" should read -- a group --; line 68: "VI" should read -- VII --.

Column 15, line 40: "prosess" should read -- process --.

Column 18, line 57: "3-(4-Nitrobenzamide)-" should read -- 3-(4-Nitrobenzamido)- --.

Column 22, line 66: "3-(4-Benzyloxbenzamido)-" should read -- 3-(4-Benzyloxybenzamido)- --.

Column 25, line 28: "sirup" should read -- syrup --; line 55: "a. 3-Nitro-4-benzyloxy-α-" should read -- a. 3-Nitro-4-benzyloxy-β- --; line 66: "sirup" should read -- syrup --.

Column 26, line 5: "zylox-α-" should read -- zyloxy-α- --; line 8: "benzlalcohol" should read -- benzylalcohol --.

UNITED STATES PATENT OFFICE
CERTIFICATE OF CORRECTION

Patent No. 4,072,760   Dated February 7, 1978

Inventor(s) Kurt Hedegaard

It is certified that error appears in the above-identified patent and that said Letters Patent are hereby corrected as shown below:

Title page, right side, last line of the Abstract: "bronchosposmolytic" should read -- bronchospasmolytic --.

Column 2, lines 23-24: "alkycarbonyl-lower" should read -- alkylcarbonyl-lower --.

Column 3, line 51: "subcalass" should read -- subclass --; lines 53-59:

"  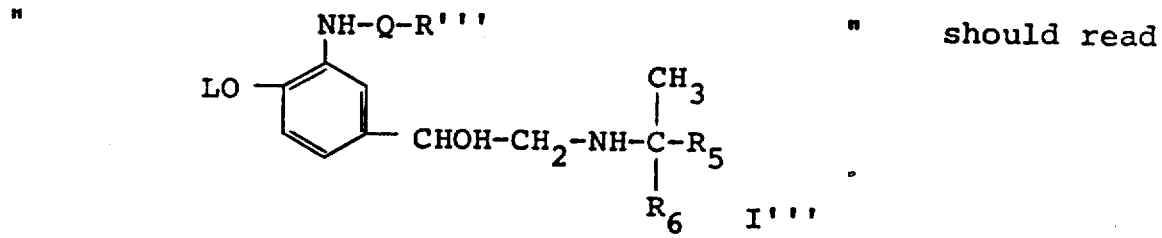   "  should read

--  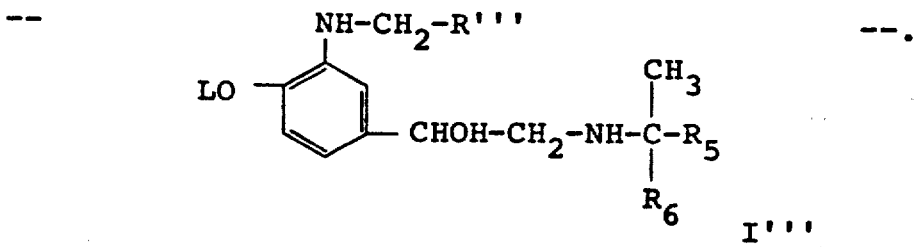   --.

Column 4, lines 13-14: "entermediates" should read -- intermediates --; line 15: "compounds" should read -- Compounds --; line 26: "way be" should read -- way by --; line 37: "inhalastion" should read -- inhalations --; line 38: "aerolos" should read -- aerosol --; line 58: "Mixtures of" should read -- Mixtures for --; line 66: "1.0 - 2 ml." should read -- 0.1 - 2 ml. --.

UNITED STATES PATENT OFFICE
CERTIFICATE OF CORRECTION

Patent No. 4,072,760　　　　　　　　Dated February 7, 1978

Inventor(s) Kurt Hedegaard

It is certified that error appears in the above-identified patent and that said Letters Patent are hereby corrected as shown below:

Column 27, line 65: "3-Nitro-4hydroxyacetophenoneone" should read -- 3-Nitro-4-hydroxyacetophenone --.

Column 28, line 64: "the" should read -- The --.

Column 29, line 29: "representative" should read -- representatives --; line 36: "incrase" should read -- increase --; line 44: "in" should read -- is --.

Column 30, line 44: "rate" should read -- rats --.

Column 31, line 5 of Table: "3-(3-Hydroxybenxylamine)-4-hy-" should read -- 3-(3-Hydroxybenzylamino)-4-hy- --; last line of Table "Saloutamol" should read -- Salbutamol --.

Signed and Sealed this

Twelfth Day of June 1979

[SEAL]

Attest:

RUTH C. MASON
Attesting Officer

DONALD W. BANNER
Commissioner of Patents and Trademarks